United States Patent
Hewitt et al.

(10) Patent No.: US 11,317,921 B2
(45) Date of Patent: May 3, 2022

(54) FILAMENTARY DEVICES FOR TREATMENT OF VASCULAR DEFECTS

(71) Applicant: SEQUENT MEDICAL, INC., Aliso Viejo, CA (US)

(72) Inventors: Todd Hewitt, Laguna Niguel, CA (US); Parker Milhous, Santa Ana, CA (US); Joseph Emery, Riverside, CA (US); Hung Tran, Midway City, CA (US); John Vu, Santa Ana, CA (US); Hussain S. Rangwala, Villa Park, CA (US); William R. Patterson, Huntington Beach, CA (US)

(73) Assignee: SEQUENT MEDICAL, INC., Aliso Viejo, CA (US)

( * ) Notice: Subject to any disclaimer, the term of this patent is extended or adjusted under 35 U.S.C. 154(b) by 82 days.

(21) Appl. No.: 16/817,032

(22) Filed: Mar. 12, 2020

(65) Prior Publication Data
US 2020/0289126 A1   Sep. 17, 2020

Related U.S. Application Data

(60) Provisional application No. 62/819,309, filed on Mar. 15, 2019.

(51) Int. Cl.
 *A61B 17/12*   (2006.01)
 *A61B 17/00*   (2006.01)

(52) U.S. Cl.
 CPC .. *A61B 17/12113* (2013.01); *A61B 17/12172* (2013.01); *A61B 17/12177* (2013.01); *A61B 2017/00526* (2013.01)

(58) Field of Classification Search
 CPC ........ A61B 17/12113; A61B 17/12172; A61B 17/12177; A61B 17/12022;
 (Continued)

(56) References Cited

U.S. PATENT DOCUMENTS

| 3,874,388 A | 4/1975 | King et al. |
| 4,282,875 A | 8/1981 | Serbinenko |

(Continued)

FOREIGN PATENT DOCUMENTS

| AU | 2009242528 | 3/2016 |
| CA | 2722037 | 10/2009 |

(Continued)

OTHER PUBLICATIONS

WO, PCT/US20/22096 ISR and Written Opinion, dated Jul. 24, 2020.

(Continued)

*Primary Examiner* — Sarah A Simpson
*Assistant Examiner* — Paige A Codrington
(74) *Attorney, Agent, or Firm* — One LLP

(57) ABSTRACT

Devices and methods for treatment of a patient's vasculature are described. Embodiments may include a permeable implant such as a permeable shell or mesh having a radially constrained state configured for delivery within a catheter lumen, an expanded state, and a plurality of elongate filaments that are woven together. The permeable implant may include a stiffer proximal portion that is configured to sit at the neck of an aneurysm. The stiffer proximal portion may include additional mesh layers on either the inside or the outside of a first permeable shell. The distal portion of the device may be softer and deformable.

18 Claims, 19 Drawing Sheets

(58) Field of Classification Search
CPC .......... A61B 17/12031; A61B 17/0057; A61B 17/12118; A61B 17/12122; A61B 17/12131; A61B 2017/00575; A61B 2017/0061; A61B 2017/00632; A61B 2017/12095; A61F 2/01; A61F 2/0105; A61F 2/0108; A61F 2/012; A61F 2/013; A61F 2002/016
USPC ........................................................ 606/200
See application file for complete search history.

(56) References Cited

U.S. PATENT DOCUMENTS

| | | |
|---|---|---|
| 4,346,712 A | 8/1982 | Handa et al. |
| 4,402,319 A | 9/1983 | Handa et al. |
| 4,619,246 A | 10/1986 | Molgaard-Nielsen et al. |
| 4,675,361 A | 6/1987 | Ward |
| 4,729,278 A | 3/1988 | Graeff |
| 4,998,539 A | 3/1991 | Delsanti |
| 5,061,275 A | 10/1991 | Wallsten et al. |
| 5,071,407 A | 12/1991 | Termin et al. |
| 5,108,407 A | 4/1992 | Geremia et al. |
| 5,122,136 A | 6/1992 | Guglielmi et al. |
| 5,154,705 A | 10/1992 | Fleischhacker et al. |
| 5,158,545 A | 10/1992 | Trudell et al. |
| 5,165,421 A | 11/1992 | Fleischhacker et al. |
| 5,263,963 A | 11/1993 | Garrison |
| 5,334,210 A | 8/1994 | Gianturco |
| 5,378,239 A | 1/1995 | Termin |
| 5,536,247 A | 7/1996 | Thornton |
| 5,562,725 A | 10/1996 | Schmitt et al. |
| 5,569,245 A | 10/1996 | Guglielmi et al. |
| 5,578,074 A | 11/1996 | Mirigian |
| 5,591,222 A | 1/1997 | Susawa et al. |
| 5,601,595 A | 2/1997 | Smith |
| 5,630,840 A | 5/1997 | Mayer |
| D380,266 S | 6/1997 | Boatman et al. |
| 5,645,559 A | 7/1997 | Hachtman et al. |
| 5,725,552 A | 3/1998 | Kotula |
| 5,725,570 A | 3/1998 | Heath |
| 5,733,294 A | 3/1998 | Forber |
| 5,749,883 A | 5/1998 | Halpern |
| 5,759,161 A | 6/1998 | Ogawa |
| 5,766,219 A | 6/1998 | Horton |
| 5,846,261 A | 12/1998 | Kotula et al. |
| 5,873,907 A | 2/1999 | Frantzen |
| 5,907,893 A | 6/1999 | Zadno-Azizi |
| 5,916,235 A | 6/1999 | Guglielmi |
| 5,925,060 A | 7/1999 | Forber |
| 5,927,345 A | 7/1999 | Samson |
| 5,928,260 A | 7/1999 | Chin et al. |
| 5,935,148 A | 8/1999 | Villar et al. |
| 5,944,733 A | 8/1999 | Engelson |
| 5,944,738 A | 8/1999 | Amplatz |
| 5,951,599 A | 9/1999 | McCrory |
| 5,964,797 A | 10/1999 | Ho |
| 5,980,554 A | 11/1999 | Lenker et al. |
| 5,984,929 A | 11/1999 | Bashiri et al. |
| 5,989,242 A | 11/1999 | Saadat et al. |
| 6,033,423 A | 3/2000 | Ken et al. |
| 6,063,070 A | 5/2000 | Eder |
| 6,063,104 A | 5/2000 | Villar et al. |
| 6,086,577 A | 7/2000 | Ken et al. |
| 6,093,199 A | 7/2000 | Brown et al. |
| 6,123,715 A | 9/2000 | Amplatz |
| 6,139,564 A | 10/2000 | Teoh et al. |
| 6,142,975 A | 11/2000 | Jalisi et al. |
| 6,152,144 A | 11/2000 | Lesh et al. |
| 6,156,061 A | 12/2000 | Wallace et al. |
| 6,159,206 A | 12/2000 | Ogawa |
| 6,168,615 B1 | 1/2001 | Ken et al. |
| 6,168,618 B1 | 1/2001 | Frantzen |
| 6,168,622 B1 | 1/2001 | Mazzocchi |
| 6,190,402 B1 | 2/2001 | Horton et al. |
| 6,193,708 B1 | 2/2001 | Ken et al. |
| 6,203,779 B1 | 3/2001 | Ricci et al. |
| 6,221,086 B1 | 4/2001 | Forber |
| 6,277,126 B1 | 8/2001 | Barry et al. |
| 6,290,721 B1 | 9/2001 | Heath |
| 6,315,709 B1 | 11/2001 | Garibaldi et al. |
| 6,325,815 B1 | 12/2001 | Kusleika |
| 6,342,068 B1 | 1/2002 | Thompson |
| 6,344,048 B1 | 2/2002 | Chin et al. |
| 6,346,117 B1 | 2/2002 | Greenhalgh |
| 6,350,270 B1 | 2/2002 | Roue |
| 6,368,338 B1 | 4/2002 | Konya |
| 6,368,339 B1 | 4/2002 | Amplatz |
| 6,375,668 B1 | 4/2002 | Gifford |
| 6,375,670 B1 | 4/2002 | Greenhalgh |
| 6,383,174 B1 | 5/2002 | Eder |
| 6,391,037 B1 | 5/2002 | Greenhalgh |
| 6,425,914 B1 | 7/2002 | Wallace et al. |
| 6,428,558 B1 | 8/2002 | Jones et al. |
| 6,447,531 B1 | 9/2002 | Amplatz |
| 6,454,780 B1 | 9/2002 | Wallace |
| 6,461,370 B1 | 10/2002 | Gray et al. |
| 6,463,317 B1 | 10/2002 | Kucharczyk |
| 6,468,266 B1 | 10/2002 | Bashiri et al. |
| 6,478,773 B1 | 11/2002 | Gandhi et al. |
| 6,500,149 B2 | 12/2002 | Gandhi et al. |
| 6,506,204 B2 | 1/2003 | Mazzocchi |
| 6,511,468 B1 | 1/2003 | Cragg et al. |
| 6,551,303 B1 | 4/2003 | Van Tassel et al. |
| 6,579,303 B2 | 6/2003 | Amplatz |
| 6,585,748 B1 | 7/2003 | Jeffree |
| 6,589,256 B2 | 7/2003 | Forber |
| 6,589,265 B1 | 7/2003 | Palmer et al. |
| 6,599,308 B2 | 7/2003 | Amplatz |
| 6,605,102 B1 | 8/2003 | Mazzocchi et al. |
| 6,605,111 B2 | 8/2003 | Bose et al. |
| 6,607,539 B1 | 8/2003 | Hayashi et al. |
| 6,613,074 B1 | 9/2003 | Mitelberg |
| 6,632,241 B1 | 10/2003 | Hancock |
| 6,635,068 B1 | 10/2003 | Dubrul et al. |
| 6,638,257 B2 | 10/2003 | Amplatz |
| 6,652,556 B1 | 11/2003 | Van Tassel et al. |
| 6,666,882 B1 | 12/2003 | Bose et al. |
| 6,669,721 B1 | 12/2003 | Bose et al. |
| 6,682,546 B2 | 1/2004 | Amplatz |
| 6,689,150 B1 | 2/2004 | Van Tassel |
| 6,689,486 B2 | 2/2004 | Ho et al. |
| 6,719,778 B1 | 4/2004 | Van Tassel et al. |
| 6,730,119 B1 | 5/2004 | Smalling |
| 6,743,236 B2 | 6/2004 | Barry et al. |
| 6,743,251 B1 | 6/2004 | Eder |
| 6,746,468 B1 | 6/2004 | Sepetka et al. |
| 6,746,890 B2 | 6/2004 | Gupta et al. |
| 6,752,826 B2 | 6/2004 | Holloway et al. |
| 6,780,196 B2 | 8/2004 | Chin et al. |
| 6,811,560 B2 | 11/2004 | Jones et al. |
| 6,818,006 B2 | 11/2004 | Douk et al. |
| 6,855,153 B2 | 2/2005 | Saadat |
| 6,855,154 B2 | 2/2005 | Abdel-Gawwad |
| 6,878,384 B2 | 4/2005 | Cruise et al. |
| 6,936,055 B1 | 8/2005 | Ken et al. |
| 6,940,209 B2 | 9/2005 | Henderson |
| 6,953,472 B2 | 10/2005 | Palmer et al. |
| 6,953,473 B2 | 10/2005 | Porter |
| 6,966,892 B2 | 11/2005 | Gandhi et al. |
| 6,994,092 B2 | 2/2006 | van der Burg et al. |
| 7,001,409 B2 | 2/2006 | Amplatz |
| 7,004,962 B2 | 2/2006 | Stinson |
| 7,011,671 B2 | 3/2006 | Welch |
| 7,044,958 B2 | 5/2006 | Douk et al. |
| 7,052,513 B2 | 5/2006 | Thompson |
| 7,083,632 B2 | 8/2006 | Avellanet et al. |
| 7,101,390 B2 | 9/2006 | Nelson |
| 7,122,043 B2 | 10/2006 | Greenhalgh et al. |
| 7,128,736 B1 | 10/2006 | Abrams et al. |
| 7,179,276 B2 | 2/2007 | Barry et al. |
| 7,182,774 B2 | 2/2007 | Barry et al. |
| 7,195,636 B2 | 3/2007 | Avellanet et al. |
| 7,198,613 B2 | 4/2007 | Gandhi et al. |
| 7,201,918 B2 | 4/2007 | Cruise |

(56) References Cited

U.S. PATENT DOCUMENTS

| | | |
|---|---|---|
| 7,229,454 B2 | 6/2007 | Tran |
| 7,229,461 B2 | 7/2007 | Chin et al. |
| 7,275,471 B2 | 10/2007 | Nishri et al. |
| 7,326,225 B2 | 2/2008 | Ferrera et al. |
| 7,329,279 B2 | 2/2008 | Haug et al. |
| 7,331,980 B2 | 2/2008 | Dubrul |
| 7,410,482 B2 | 8/2008 | Murphy |
| 7,419,503 B2 | 9/2008 | Pulnev et al. |
| 7,490,396 B2 | 2/2009 | Bradley |
| 7,524,319 B2 | 4/2009 | Dubrul |
| 7,569,066 B2 | 8/2009 | Gerberding |
| 7,573,382 B2 | 8/2009 | Choubey et al. |
| 7,575,582 B2 | 8/2009 | Gandhi et al. |
| 7,578,826 B2 | 8/2009 | Gandhi et al. |
| 7,597,704 B2 | 10/2009 | Frazier et al. |
| 7,648,532 B2 | 1/2010 | Greenhalgh et al. |
| 7,695,488 B2 | 4/2010 | Berenstein |
| 7,722,637 B2 | 5/2010 | Barry et al. |
| 7,745,732 B2 | 6/2010 | Michael et al. |
| 7,806,919 B2 | 10/2010 | Bloom et al. |
| 7,862,577 B2 | 1/2011 | Gray et al. |
| 7,942,925 B2 | 5/2011 | Yodaf |
| 7,989,703 B2 | 8/2011 | Schaffer |
| 8,043,326 B2 | 10/2011 | Hancock |
| 8,043,329 B2 | 10/2011 | Khairkhahan |
| 8,066,757 B2 | 11/2011 | Ferrera et al. |
| 8,142,456 B2 | 3/2012 | Rosqueta et al. |
| 8,182,506 B2 | 5/2012 | Fitz et al. |
| 8,192,480 B2 | 6/2012 | Tieu et al. |
| 8,313,505 B2 | 11/2012 | Amplatz et al. |
| 8,398,670 B2 | 3/2013 | Amplatz |
| 8,430,012 B1 | 4/2013 | Marchand |
| 8,506,619 B2 | 8/2013 | Ortiz et al. |
| 8,551,132 B2 | 10/2013 | Eskridge et al. |
| 8,597,320 B2 | 12/2013 | Sepetka |
| 8,597,323 B1 | 12/2013 | Plaza et al. |
| 8,715,338 B2 | 5/2014 | Frid |
| 8,728,117 B1 | 5/2014 | Janardhan et al. |
| 8,758,395 B2 | 6/2014 | Kleshinski et al. |
| 8,795,330 B1 * | 8/2014 | Janardhan ............... B26F 3/004 606/213 |
| 8,840,735 B2 | 9/2014 | Schaffer |
| 8,845,679 B1 | 9/2014 | Janardhan et al. |
| 9,078,658 B2 | 7/2015 | Hewitt et al. |
| 9,198,668 B2 | 12/2015 | Theobald et al. |
| 9,198,670 B2 | 12/2015 | Hewitt et al. |
| 9,259,337 B2 | 2/2016 | Cox et al. |
| 9,272,323 B2 | 3/2016 | Schaffer |
| 9,295,473 B2 | 3/2016 | Hewitt et al. |
| 9,492,174 B2 | 11/2016 | Hewitt et al. |
| 9,504,588 B2 | 11/2016 | Sadisivan et al. |
| 9,597,087 B2 | 3/2017 | Marchand et al. |
| 9,629,635 B2 | 4/2017 | Hewitt et al. |
| 9,955,976 B2 * | 5/2018 | Hewitt ............. A61B 17/12031 |
| 10,136,896 B2 | 11/2018 | Hewitt et al. |
| 10,470,773 B2 * | 11/2019 | Maguire .......... A61B 17/12109 |
| 10,952,739 B2 | 3/2021 | Plaza et al. |
| 2001/0031981 A1 | 10/2001 | Evans et al. |
| 2002/0065552 A1 | 5/2002 | Jayaraman et al. |
| 2002/0103542 A1 | 8/2002 | Bilbo |
| 2002/0111647 A1 | 8/2002 | Khairkhahan et al. |
| 2002/0143349 A1 | 10/2002 | Gifford, III et al. |
| 2002/0143361 A1 | 10/2002 | Douk et al. |
| 2002/0156499 A1 | 10/2002 | Konya et al. |
| 2002/0169473 A1 | 11/2002 | Sepetka et al. |
| 2002/0183787 A1 | 12/2002 | Wahr et al. |
| 2002/0187288 A1 | 12/2002 | Lim et al. |
| 2003/0012816 A1 | 1/2003 | West et al. |
| 2003/0028209 A1 | 2/2003 | Teoh et al. |
| 2003/0171739 A1 | 9/2003 | Murphy et al. |
| 2003/0171774 A1 | 9/2003 | Freudenthal et al. |
| 2003/0181942 A1 | 9/2003 | Sutton et al. |
| 2003/0187473 A1 | 10/2003 | Berenstein et al. |
| 2003/0199913 A1 | 10/2003 | Dubrul et al. |
| 2004/0059370 A1 | 3/2004 | Green, Jr. et al. |
| 2004/0098027 A1 | 5/2004 | Tech et al. |
| 2004/0111147 A1 | 6/2004 | Rabkin et al. |
| 2004/0122367 A1 | 6/2004 | Sculati et al. |
| 2004/0143239 A1 | 7/2004 | Zhou et al. |
| 2004/0158311 A1 | 8/2004 | Berhow |
| 2004/0172053 A1 | 9/2004 | Barry et al. |
| 2004/0186562 A1 | 9/2004 | Cox |
| 2004/0193206 A1 | 9/2004 | Gerberding et al. |
| 2004/0193208 A1 | 9/2004 | Talpade et al. |
| 2004/0220563 A1 | 11/2004 | Eder |
| 2004/0260333 A1 | 12/2004 | Dubrul et al. |
| 2005/0021075 A1 | 1/2005 | Bonnette et al. |
| 2005/0033408 A1 | 2/2005 | Jones et al. |
| 2005/0053782 A1 | 3/2005 | Sen et al. |
| 2005/0096728 A1 | 5/2005 | Ramer |
| 2005/0112349 A1 | 5/2005 | Laurencin et al. |
| 2005/0113868 A1 | 5/2005 | Devellian et al. |
| 2005/0119684 A1 | 6/2005 | Gutterman et al. |
| 2005/0133046 A1 | 6/2005 | Becker et al. |
| 2005/0149173 A1 | 7/2005 | Hunter et al. |
| 2005/0216052 A1 | 9/2005 | Mazzocchi et al. |
| 2005/0222489 A1 | 10/2005 | Rahdert et al. |
| 2005/0228422 A1 | 10/2005 | Machold et al. |
| 2005/0228434 A1 | 10/2005 | Amplatz et al. |
| 2005/0267516 A1 | 12/2005 | Soleimani et al. |
| 2005/0277978 A1 | 12/2005 | Greenhalgh |
| 2006/0009798 A1 | 1/2006 | Callister et al. |
| 2006/0009799 A1 | 1/2006 | Kleshinski et al. |
| 2006/0009800 A1 | 1/2006 | Christianson et al. |
| 2006/0052815 A1 | 3/2006 | Fitz et al. |
| 2006/0052816 A1 | 3/2006 | Bates et al. |
| 2006/0064151 A1 | 3/2006 | Guterman et al. |
| 2006/0083721 A1 | 4/2006 | Cohen et al. |
| 2006/0116708 A1 | 6/2006 | Ogawa et al. |
| 2006/0135947 A1 | 6/2006 | Soltesz et al. |
| 2006/0155323 A1 | 7/2006 | Porter et al. |
| 2006/0178694 A1 | 8/2006 | Greenhalgh et al. |
| 2006/0200192 A1 | 9/2006 | Fitz et al. |
| 2006/0200234 A1 | 9/2006 | Hines |
| 2006/0212055 A1 | 9/2006 | Karabey et al. |
| 2006/0217799 A1 | 9/2006 | Mailander et al. |
| 2006/0235464 A1 | 10/2006 | Avellanet et al. |
| 2006/0247680 A1 | 11/2006 | Amplatz et al. |
| 2006/0252984 A1 | 11/2006 | Rahdert et al. |
| 2006/0253149 A1 | 11/2006 | Gandhi et al. |
| 2006/0271086 A1 | 11/2006 | Ramzipoor et al. |
| 2007/0021816 A1 | 1/2007 | Rudin |
| 2007/0031584 A1 | 2/2007 | Roth |
| 2007/0061006 A1 | 3/2007 | Desatnik et al. |
| 2007/0088387 A1 | 4/2007 | Eskridge et al. |
| 2007/0100419 A1 | 5/2007 | Licata et al. |
| 2007/0106323 A1 | 5/2007 | Barry et al. |
| 2007/0112380 A1 | 5/2007 | Figulla et al. |
| 2007/0142906 A1 | 6/2007 | Figulla et al. |
| 2007/0144124 A1 | 6/2007 | Schewe et al. |
| 2007/0167911 A1 | 7/2007 | Gandhi et al. |
| 2007/0167980 A1 | 7/2007 | Figulla et al. |
| 2007/0173928 A1 | 7/2007 | Morsi |
| 2007/0203062 A1 | 8/2007 | Ellis-Behnke et al. |
| 2007/0208373 A1 | 9/2007 | Zaver et al. |
| 2007/0208376 A1 | 9/2007 | Meng |
| 2007/0225760 A1 | 9/2007 | Moszner et al. |
| 2007/0233186 A1 | 10/2007 | Meng |
| 2007/0255388 A1 | 11/2007 | Rudakov et al. |
| 2007/0265656 A1 | 11/2007 | Amplatz et al. |
| 2007/0288083 A1 | 12/2007 | Hines |
| 2008/0033341 A1 | 2/2008 | Grad |
| 2008/0033366 A1 | 2/2008 | Matson |
| 2008/0033475 A1 | 2/2008 | Meng |
| 2008/0033478 A1 | 2/2008 | Meng |
| 2008/0119886 A1 * | 5/2008 | Greenhalgh ..... A61B 17/12022 606/200 |
| 2008/0195139 A1 | 8/2008 | Donald et al. |
| 2008/0200945 A1 | 8/2008 | Amplatz et al. |
| 2008/0221600 A1 | 9/2008 | Dieck et al. |
| 2008/0228215 A1 | 9/2008 | Strauss et al. |
| 2009/0025820 A1 | 1/2009 | Adams |
| 2009/0062812 A1 | 3/2009 | Fitz et al. |
| 2009/0062834 A1 | 3/2009 | Moftakhar |

(56) References Cited

U.S. PATENT DOCUMENTS

| | | |
|---|---|---|
| 2009/0062841 A1 | 3/2009 | Amplatz et al. |
| 2009/0082803 A1 | 3/2009 | Adams et al. |
| 2009/0099647 A1 | 4/2009 | Glimsdale et al. |
| 2009/0112305 A1 | 4/2009 | Goldmann et al. |
| 2009/0132024 A1 | 5/2009 | Berkhoff |
| 2009/0227976 A1 | 9/2009 | Calabria |
| 2009/0275974 A1 | 11/2009 | Marchand |
| 2009/0287291 A1 | 11/2009 | Becking et al. |
| 2009/0287294 A1 | 11/2009 | Rosqueta et al. |
| 2009/0318948 A1 | 12/2009 | Linder et al. |
| 2010/0023048 A1 | 1/2010 | Mach |
| 2010/0069948 A1 | 3/2010 | Veznedaroglu et al. |
| 2010/0094409 A1 | 4/2010 | Barker et al. |
| 2010/0106235 A1 | 4/2010 | Kariniemi et al. |
| 2011/0022149 A1 | 1/2011 | Cox |
| 2011/0029008 A1 | 2/2011 | Gesswein |
| 2011/0046658 A1 | 2/2011 | Connor et al. |
| 2011/0046719 A1 | 2/2011 | Frid |
| 2011/0054515 A1 | 3/2011 | Bridgeman |
| 2011/0082493 A1 | 4/2011 | Samson et al. |
| 2011/0152823 A1 | 6/2011 | Mohiuddin et al. |
| 2011/0152993 A1* | 6/2011 | Marchand ........ A61B 17/12172 623/1.2 |
| 2011/0202085 A1 | 8/2011 | Loganathan et al. |
| 2011/0208227 A1 | 8/2011 | Becking |
| 2011/0208233 A1 | 8/2011 | McGuckin |
| 2011/0224776 A1 | 9/2011 | Sepekta et al. |
| 2011/0295298 A1 | 12/2011 | Moszner |
| 2011/0319926 A1 | 12/2011 | Becking |
| 2012/0065667 A1 | 3/2012 | Javois et al. |
| 2012/0143237 A1 | 6/2012 | Cam |
| 2012/0165919 A1 | 6/2012 | Cox |
| 2012/0197283 A1 | 8/2012 | Marchand et al. |
| 2012/0271337 A1 | 10/2012 | Figulla et al. |
| 2012/0283768 A1 | 11/2012 | Cox |
| 2012/0330341 A1* | 12/2012 | Becking ........... A61B 17/12172 606/191 |
| 2013/0116722 A1 | 5/2013 | Aboytes et al. |
| 2013/0123830 A1 | 5/2013 | Becking et al. |
| 2013/0211495 A1 | 8/2013 | Halden et al. |
| 2013/0245667 A1 | 9/2013 | Marchand et al. |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2014/0005713 A1 | 1/2014 | Bowman et al. |
| 2014/0005714 A1 | 1/2014 | Quick et al. |
| 2014/0018841 A1 | 1/2014 | Peiffer et al. |
| 2014/0052233 A1 | 2/2014 | Cox et al. |
| 2014/0074151 A1 | 3/2014 | Tischler et al. |
| 2014/0135734 A1 | 5/2014 | Dakin et al. |
| 2014/0135817 A1 | 5/2014 | Tischler et al. |
| 2014/0172001 A1 | 6/2014 | Becking et al. |
| 2014/0257361 A1 | 9/2014 | Prom |
| 2015/0133989 A1 | 5/2015 | Lubock et al. |
| 2015/0182674 A1 | 7/2015 | Schaffer |
| 2015/0272589 A1 | 10/2015 | Lorenzo |
| 2015/0374483 A1* | 12/2015 | Janardhan ............... A61M 1/74 606/200 |
| 2016/0030052 A1 | 2/2016 | Cragg et al. |
| 2016/0192941 A1 | 7/2016 | Hewitt et al. |
| 2016/0249934 A1* | 9/2016 | Hewitt ............. A61B 17/12145 606/200 |
| 2016/0249937 A1 | 9/2016 | Marchand et al. |
| 2016/0262769 A1 | 9/2016 | Cragg et al. |
| 2016/0324528 A1 | 11/2016 | Hebert et al. |
| 2016/0324668 A1* | 11/2016 | Wallace ..................... A61F 2/90 |
| 2016/0335757 A1 | 11/2016 | Florent et al. |
| 2016/0367260 A9 | 12/2016 | Hewitt et al. |
| 2017/0079662 A1 | 3/2017 | Rhee et al. |
| 2017/0095254 A1 | 4/2017 | Hewitt et al. |
| 2017/0128077 A1 | 5/2017 | Hewitt et al. |
| 2017/0224350 A1 | 8/2017 | Shimizu et al. |
| 2017/0245862 A1 | 8/2017 | Cox et al. |
| 2018/0000489 A1 | 1/2018 | Marchand et al. |
| 2018/0206849 A1 | 7/2018 | Hewitt et al. |
| 2018/0206851 A1 | 7/2018 | Walzman |
| 2018/0338767 A1 | 11/2018 | Dasnurkar et al. |
| 2019/0192167 A1* | 6/2019 | Lorenzo .......... A61B 17/12113 |
| 2019/0223881 A1 | 7/2019 | Hewitt et al. |
| 2019/0298364 A1 | 10/2019 | Walsh et al. |
| 2020/0113576 A1* | 4/2020 | Gorochow ....... A61B 17/12113 |
| 2021/0153871 A1* | 5/2021 | Griffin ............. A61B 17/12031 |

FOREIGN PATENT DOCUMENTS

| | | |
|---|---|---|
| CN | 106974691 | 7/2017 |
| EP | 0706876 | 7/2000 |
| EP | 0808138 | 5/2005 |
| EP | 1576929 | 9/2005 |
| EP | 1844717 | 10/2007 |
| EP | 1923019 | 5/2008 |
| EP | 2055263 | 6/2009 |
| EP | 2258275 | 12/2011 |
| EP | 2157937 | 3/2017 |
| FR | 2333169 | 6/1997 |
| JP | 52141092 | 11/1977 |
| JP | H4-47415 | 4/1992 |
| WO | WO 95/30384 | 11/1995 |
| WO | WO 96/01591 | 1/1996 |
| WO | WO 97/26939 | 7/1997 |
| WO | WO 99/03404 | 1/1999 |
| WO | WO 99/05977 | 2/1999 |
| WO | WO 99/62432 | 12/1999 |
| WO | WO 01/45571 | 6/2001 |
| WO | WO 01/93782 | 12/2001 |
| WO | WO 02/00139 | 1/2002 |
| WO | WO 03/011151 | 2/2003 |
| WO | WO 03/032818 | 4/2003 |
| WO | WO 03/063732 | 8/2003 |
| WO | WO 2004/047649 | 6/2004 |
| WO | WO 2004/093742 | 11/2004 |
| WO | WO 2005/117718 | 12/2005 |
| WO | WO 2006/026744 | 3/2006 |
| WO | WO 2006/055683 | 5/2006 |
| WO | WO 2007/006139 A1 | 1/2007 |
| WO | WO 2007/096183 | 8/2007 |
| WO | WO 2008/151204 | 12/2008 |
| WO | WO 2009/036219 | 3/2009 |
| WO | WO 2009/121006 | 10/2009 |
| WO | WO 2009/126747 | 10/2009 |
| WO | WO 2009/132045 | 10/2009 |
| WO | WO 2009/134337 | 11/2009 |
| WO | WO 2009/135166 | 11/2009 |
| WO | WO 2010/134914 | 11/2010 |
| WO | WO 2011/057002 | 5/2011 |
| WO | WO 2013/102848 | 7/2013 |
| WO | WO 2014/169261 | 10/2014 |
| WO | WO 2015/160721 | 10/2015 |
| WO | WO 2015/171268 | 11/2015 |
| WO | WO 2015/192019 | 12/2015 |
| WO | WO 2017/153603 A1 | 9/2017 |
| WO | WO 2018/051187 A1 | 3/2018 |
| WO | WO 2019/040494 A1 | 2/2019 |

OTHER PUBLICATIONS

A Complete Microcatheter Portfolio; A Broad Selection of Microcatheters. Boston Scientific Brochure 2007.

Allen et al., "Micromachine Wedge Stepping Motor," pp. 1-6, Nov. 12-20, 1998 ASME International Mechanical Engineering Congress, Anaheim, CA.

Altes et al., "Creation of Saccular Aneurysms in the Rabbit: A model Suitable for Testing Endovascular Devices," American Roentgen Ray Society, Feb. 2000.

Ansari et al., "Thrombosis of a Fusiform Intracranial Aneurysm Induced by Overlapping Neuroform Stents: Case Report," *Neurosurgery*, E950-E951 vol. 60, No. 5, May 2007.

Atritech Press Release, Minneapolis, Jun. 18, 2007 "Atritech Announces Intellectual Property Acquisition, Transaction Establishes Company as leader in Left Atrial Appendage Market."

(56) References Cited

OTHER PUBLICATIONS

Caroff, J. et al., "Woven Endobridge (WEB) Device for endovascular treatment of ruptured intracranial wide-neck aneurysms: a single-center experience," Neuroradiology, 56(9):755-761 (Sep. 2014).
Caroff, J. et al., "Role of C-Arm VasoCT in the Use of Endovascular WEB Flow Disruption in Intracranial Aneurysm Treatment," AJNR Am. J. Neuroradiol. 35(7):1353-1357 (Jul. 2014).
Colla, R. et al., "Treatment of Wide-Neck Basilar Tip Aneurysms Using the Web II Device," The Neuroradiology Journal 26(6):669-677 (Dec. 2013).
De Backer, O. et al., "Percutaneous left atrial appendage occlusion for stroke prevention in atrial fibrillation: an update," Open Heart, 4:1-14 (2013).
Ding, Y.H. et al., "The Woven EndoBridge: A New Aneurysm Occlusion Device," AJNR Am. J. Neruradiol. 32:607-611 (Mar. 2011).
Duerig, T.W., "The Use of Superelasticity in Modern Medicine," MRS Bulletin, p. 101-104 (Feb. 2002).
Fiorella, D. et al., "Interobserver variability in the assessment of aneurysm occlusion with the WEB aneurysm embolization system," J. NeuroIntervent. Surg. Jul. 1, 2014, pii: neurintsurg-2014-011251. doi: 10.1136/neurintsurg-2014-011251 [Epub ahead of print].
Fort Wayne Metals HHS Tube brochure, p. 28-29 (2009), Fort Wayne, Indiana, www.oldsite.fwmetals.com.
Grabenwoger et al., "Endothelialization of Biosynthetic vascular Prosthesis After Laser Perforation,"Ann Thorac Surg, 66:S110-S114 (1998).
Guider Softip XF Guide Catheters Brochure, Boston Scientific Corporation 2004.
Gupta et al., "Nitinol Thin Film Three Dimensional Devices-Fabrication and Applications," From: SMST-2003: Proceedings of the International Conference on Shape Memory and Superelastic Technologies Published: 2004.
Hill et al., "Initial Results of the AMPLATZER® Vascular Plug in the treatment of Congenital Heart Disease," Technology and Services, Business Briefing: US Cardiology, pp. 1-3 (2004).
Jeffree et al., "The Porus, Guidewire-Directed, Detachable Aneurysm Liner: A New Concept in the Endovascular Treatment of Intracranial Aneurysms," AJNR Am J Neuradiol 20:774-779 (May 1999).
Kallmes et al., "A New Endoluminal, Flow-Disrupting Device for Treatment of Saccular Eneurysms," Stroke, Journal of the American Heart Association 38:1-7 (2007).
Klisch, J. et al., "The Woven EndoBridge Cerebral Aneurysm Embolization Device (Web II): initial clinical experience," Neuroradiology 53:599-607 (2011).
Kónya, A. et al., "Preliminary Results with a New Vascular Basket Occluder in Swine," JVIR, 10(8):1043-1049 (1999).
Kwon et al., "Preliminary Results of the Luna Aneurysm Embolization System in a Rabbit Model: A New Intrasaccular Aneurysm Occlusion Device," AJNR Am J Neuroradiol, 32:602-606 (Mar. 2011).
Lendlein, A. et al., "Shape-Memory Polymers," Angew. Chem. Int. Ed., 41:2034-2057 (2002).
Lendlein, A. et al., "Biodegradable, Elastic Shape-Memory Polymers for Potential Biomedical Applications," Science 296:1673-1676 (May 31, 2002).
Lieber, B.B. et al., "The Role of Blood Impulse in Cerebral Aneurysm Coil Compaction: Effect of Aneurysm Neck Size," IMECE2003-43099, Proceedings of IMECE '03, 2003 ASME International Mechanical Engineering Congress, Washington, D.C. (Nov. 15-21, 2003).
Liu, C. et al., "Review of progress in shape-memory polymers," J. Mater. Chem. 17:1543-1558 (2007).
Lubicz, B. et al., "WEB Device for Endovascular Treatment of Wide-Neck Bifurcation Aneurysms," AJNR Am. J. Neuroradiol. 34(6):1209-1214 (Jun.-Jul. 2013).
Lubicz, B. et al., "WEB-DL Endovascular Treatment of Wide-Neck Bifurcation Aneurysms: Short- and Midterm Results in a European Study," AJNR Am. J. Neuroradiol. 35(3):432-438 (Mar. 2014). doi: 10.3174/ajnr.A3869. Epub Jan. 23, 2014.
Major, S. et al., "Life of Nitinol Drawn Filed Wires with Ag or Au Core for Medical Application," International Journal of Mechanics 2(7):73-80 (2013).
Matinlinna et al., "An Introduction to Silanes and Their Clinical Applications in Dentistry," The International Journal of Prosthodontics, 17(2):155-164 (2004).
Mine et al., "Intrasaccular flow-diversion for treatment of intracranial aneurysms: the Woven EndoBridge," Expert Rev. Med. Devices11 (3): 315-325 (May 2014). doi: 10.1586/17434440.2014.907741. Epub Apr. 2, 2014.
Nakayama et al., "Development of Microporous Covered Stents: Geometrical Design of the Luminal Surface," The International Journal of Artificial Organs, 28(6):600-608 (2005).
Nemat-Nasser, S. et al., "Superelastic and cyclic response of NiTi SMA at various strain rates and temperatures," Mechanics of Materials 38:463-474 (2006).
Nishi et al., "Embolization of experimental aneurysms using a heparin-loaded stent graft with micropores," Cardiovascular Radiation Medicine 4:29-33 (2003).
Nishi et al., "Occlusion of Experimental Aneurysms with Heparin-Loaded, Microporous Stent Grafts," Neurosurgery 53(6):1397-1405 (Dec. 2003).
Papagiannaki, C. et al., "WEB Intrasaccular Flow Disruptor—Prospective, Multicenter Experience in 83 Patients with 85 Aneurysms," AJNR Am. J. Neuroradiol. 35(11):2106-2111 (Nov.-Dec. 2014). 35(11):2106-11. doi: 10.3174/ajnr.A4028. Epub Jul. 3, 2014.
Park, J. et al., "Percutaneous Left Atrial Appendage Transcatheter Occlusion (PLAATO) for Stroke Prevention in Atrial Fibrillation: 2-Year Outcome," J Invasive. Cardiol., 21(9):446-450 (2009).
Pelton, A.R. et al., "Optimisation of processing and properties of medical grade Nitinol wire," Min. Invas. Ther. & Allied Technol. 9(1):107-118 (2000).
Pham, Q. et al., "Electrospinning of Polymeric Nanofibers for Tissue Engineering Applications: A Review," Tissue Engr 12(5):1197-1211 (1996).
Pierot, L. et al., "Intrasaccular Flow-Disruption Treatment of Intracranial Aneurysms: Preliminary Results of a Multicenter Clinical Study," AJNR Am J Neuroradiol. 33(7):1232-1238 (Aug. 2012). doi: 10.3174/ajnr.A3191. Epub Jun. 7, 2012.
Pierot, L. et al., "Endovascular WEB Flow Disruption in Middle Cerebral Artery Aneurysms: Preliminary Feasibility, Clinical, and Anatomical Results in a Multicenter Study," Neurosurgery 73(1):27-35 (Jul. 2013).
Pierot, L. et al., "Role, safety, and efficacy of WEB flow disruption: a review," EJMINT Invited Review, 2014: 1419000139 (May 8, 2014).
Peirot, L. et al., "WEB Treatment of Intracranial Aneurysms: Feasiblity, Complications, and 1-Month Safety Results with the Web DL and WEB SL/SLS in the French Observatory," AJNR Am J Neuroradiol. Feb. 5, 2015 [Epub ehead ofprint].
Romero, J. et al., "Left Atrial Appendage Closure Devices," Clinical Medicine Insights: Cardiology, 8:45-52 (2014).
Rottiers, W. et al., "Shape Memory Materials and their applications," in Korolev's readings: conference proceedings, pp. 250-250 (2011).
Salamat et al., "Experimental Evaluation of a New Transcatheter Vascular Embolization Device in the Swine Model," J Vasc Interv Radiol, 12:301-311 (2002).
Schaffer, J.E. et al., "Engineering Characteristics of Drawn Filled Nitinol Tube," SMST-2003: Proceedings of the International Conference on Shape Memory and Superelastic Technologies (ASM International), pp. 109-118 (2004).
Schmitz-Rode, T. et al., "Self-expandable spindle for transcatheter vascular occlusion: in vivo experiments. Work in progress." Radiology 188:95-100 (Jul. 1993).
Simgen, A. et al., "Evaluation of a newly designed flow diverter for the treatment of intracranial aneurysms in an elastase-induced aneurysm model, in New Zealand white rabbits," Neuroradiology 56:129-137 (2014).
Spelle, L. et al., "Letter to the Editor," Neuroradiol J. Jun. 2014; 27(3):369. doi: 10.15274/NRJ-2014-10048. Epub Jun. 17, 2014.

(56) References Cited

OTHER PUBLICATIONS

Stoeckel, D. et al., "Self-expanding nitinol stents: material and design considerations," *Eur. Radiol.* 14:292-301 (2004).
Turk, A. et al., "Evaluation of the TriSpan Neck Bridge Device for the Treatment of Wide-Necked Aneurysms: An Experimental Study in Canines, Editorial Comment: An Experimental Study in Canines," *Stroke* 32:492-497 (Feb. 2001).
Wallner, A.K. et al., "Coiling after Treatment with the Woven EndoBridge Cerebral Aneurysm Embolization Device," *Interventional Neuroradiology* 18:208-212 (2012).
Yeow, W.L. et al., Device- and LAA-Specific Characteristics for Successful LAA Closures: Tips and Tricks, *Intervent. Cardiol. Clin.*, 3:239-254 (2014).
Zimmermann et al., "Patent Foramen Oval Closure With the SeptRx Device, Initial Experience with the First "In-Tunnel" Device," *JACC Cardiovascular Interventions* vol. 3, No. 9., 2010.
International Search Report and Written Opinion dated Oct. 31, 2008 for International Application No. PCT/US2008/065694.
International Search Report and Written Opinion dated Nov. 26, 2009 for International Application No. PCT/US2009/042592.
International Search Report and Written Opinion dated Jul. 28, 2011 for International Application No. PCT/US2010/055494.
International Search Report and Written Opinion dated Jul. 21, 2015 for International Application No. PCT/US2015/025609.
International Search Report and Written Opinion dated Jan. 11, 2016 for International Application No. PCT/US2015/025613.
Extended European Search Report dated Jul. 30, 2014, in EP Appl No. EP 10829110 filed Nov. 4, 2010.
Official Action dated Mar. 8, 2019, in JP Appl. No. 2016-562549 filed Jun. 5, 2015.
WO, PCT/US20/22275 ISR and Written Opinion, dated Jun. 10, 2020.
WO, PCT/US20/22364 ISR and Written Opinion, dated Jun. 11, 2020.
WO, PCT/US20/22319 ISR and Written Opinion, dated Jun. 15, 2020.
U.S. Appl. No. 16/815,911 Non-Final Office Action, dated Oct. 15, 2021.

* cited by examiner

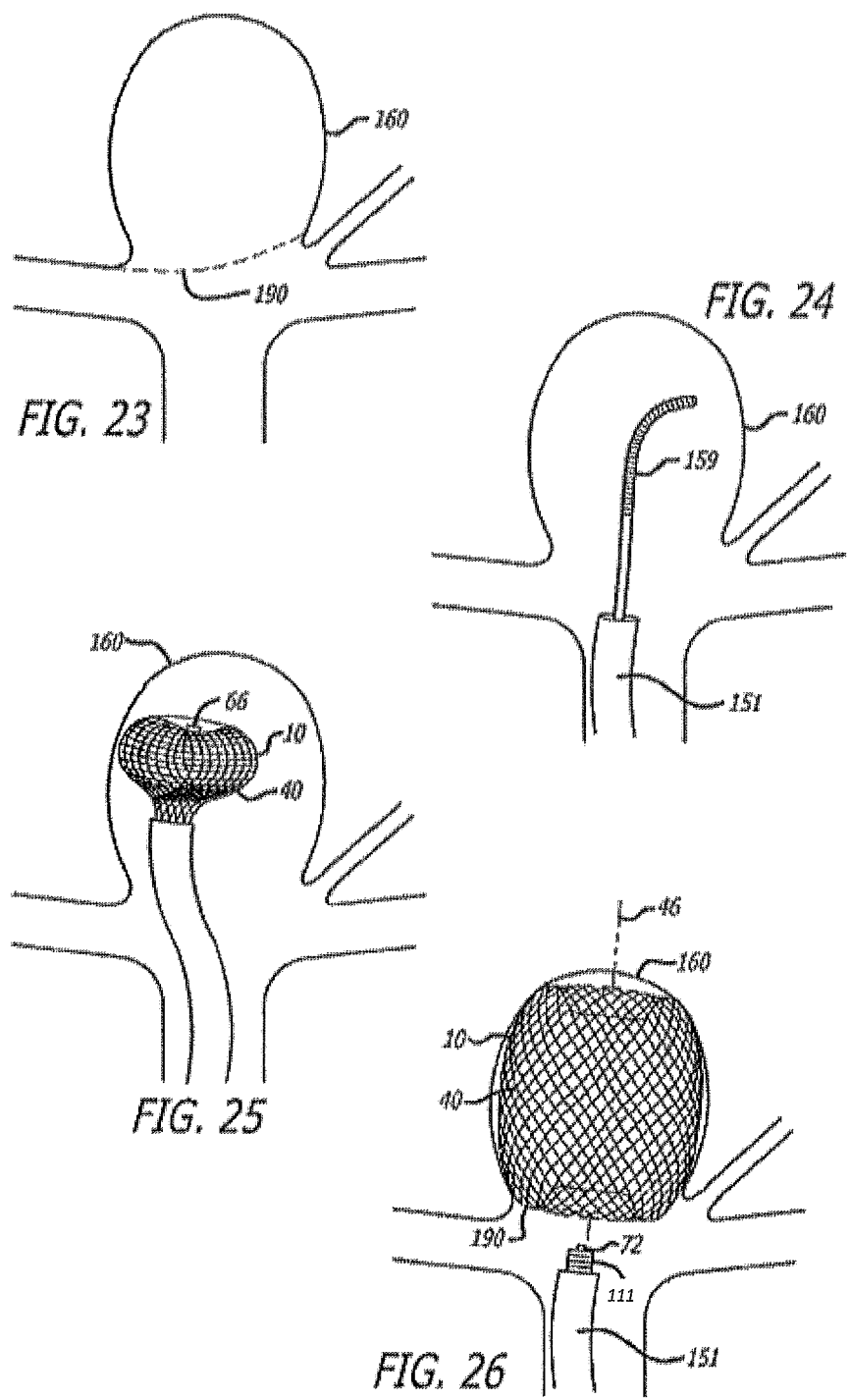

FILAMENTARY DEVICES FOR TREATMENT OF VASCULAR DEFECTS

CROSS-REFERENCE TO RELATED APPLICATIONS

This application claims the benefit of priority under 35 U.S.C. § 119(e) from U.S. Provisional Application Ser. No. 62/819,309, filed Mar. 15, 2019, which is hereby incorporated by reference in its entirety for all purposes.

STATEMENT REGARDING FEDERALLY SPONSORED RESEARCH OR DEVELOPMENT

Not applicable.

FIELD OF THE INVENTION

Embodiments of devices and methods herein are directed to blocking a flow of fluid through a tubular vessel or into a small interior chamber of a saccular cavity or vascular defect within a mammalian body. More specifically, embodiments herein are directed to devices and methods for treatment of a vascular defect of a patient including some embodiments directed specifically to the treatment of cerebral aneurysms of patients.

BACKGROUND

The mammalian circulatory system is comprised of a heart, which acts as a pump, and a system of blood vessels which transport the blood to various points in the body. Due to the force exerted by the flowing blood on the blood vessel the blood vessels may develop a variety of vascular defects. One common vascular defect known as an aneurysm results from the abnormal widening of the blood vessel. Typically, vascular aneurysms are formed as a result of the weakening of the wall of a blood vessel and subsequent ballooning and expansion of the vessel wall. If, for example, an aneurysm is present within an artery of the brain, and the aneurysm should burst with resulting cranial hemorrhaging, death could occur.

Surgical techniques for the treatment of cerebral aneurysms typically involve a craniotomy requiring creation of an opening in the skull of the patient through which the surgeon can insert instruments to operate directly on the patient's brain. For some surgical approaches, the brain must be retracted to expose the parent blood vessel from which the aneurysm arises. Once access to the aneurysm is gained, the surgeon places a clip across the neck of the aneurysm thereby preventing arterial blood from entering the aneurysm. Upon correct placement of the clip the aneurysm will be obliterated in a matter of minutes. Surgical techniques may be effective treatment for many aneurysms. Unfortunately, surgical techniques for treating these types of conditions include major invasive surgical procedures which often require extended periods of time under anesthesia involving high risk to the patient. Such procedures thus require that the patient be in generally good physical condition in order to be a candidate for such procedures.

Various alternative and less invasive procedures have been used to treat cerebral aneurysms without resorting to major surgery. One approach to treating aneurysms without the need for invasive surgery involves the placement of sleeves or stents into the vessel and across the region where the aneurysm occurs. Such devices maintain blood flow through the vessel while reducing blood pressure applied to the interior of the aneurysm. Certain types of stents are expanded to the proper size by inflating a balloon catheter, referred to as balloon expandable stents, while other stents are designed to elastically expand in a self-expanding manner. Some stents are covered typically with a sleeve of polymeric material called a graft to form a stent-graft. Stents and stent-grafts are generally delivered to a preselected position adjacent a vascular defect through a delivery catheter. In the treatment of cerebral aneurysms, covered stents or stent-grafts have seen very limited use due to the likelihood of inadvertent occlusion of small perforator vessels that may be near the vascular defect being treated.

In addition, current uncovered stents are generally not sufficient as a stand-alone treatment. In order for stents to fit through the microcatheters used in small cerebral blood vessels, their density is usually reduced such that when expanded there is only a small amount of stent structure bridging the aneurysm neck. Thus, they do not block enough flow to cause clotting of the blood in the aneurysm and are thus generally used in combination with vaso-occlusive devices, such as the coils discussed above, to achieve aneurysm occlusion.

Some procedures involve the delivery of embolic or filling materials into an aneurysm. The delivery of such vaso-occlusion devices or materials may be used to promote hemostasis or fill an aneurysm cavity entirely. Vaso-occlusion devices may be placed within the vasculature of the human body, typically via a catheter, either to block the flow of blood through a vessel with an aneurysm through the formation of an embolus or to form such an embolus within an aneurysm stemming from the vessel. A variety of implantable, coil-type vaso-occlusion devices are known. The coils of such devices may themselves be formed into a secondary coil shape, or any of a variety of more complex secondary shapes. Vaso-occlusive coils are commonly used to treat cerebral aneurysms but suffer from several limitations including poor packing density, compaction due to hydrodynamic pressure from blood flow, poor stability in wide-necked aneurysms, and complexity and difficulty in the deployment thereof as most aneurysm treatments with this approach require the deployment of multiple coils. Coiling is less effective at treating certain physiological conditions, such as wide neck cavities (e.g. wide neck aneurysms) because there is a greater risk of the coils migrating out of the treatment site.

A number of aneurysm neck bridging devices with defect spanning portions or regions have been attempted, however, none of these devices have had a significant measure of clinical success or usage. A major limitation in their adoption and clinical usefulness is the inability to position the defect spanning portion to assure coverage of the neck. Existing stent delivery systems that are neurovascular compatible (i.e. deliverable through a microcatheter and highly flexible) do not have the necessary rotational positioning capability. Another limitation of many aneurysm bridging devices described in the prior art is the poor flexibility. Cerebral blood vessels are tortuous, and a high degree of flexibility is required for effective delivery to most aneurysm locations in the brain.

What has been needed are devices and methods for delivery and use in small and tortuous blood vessels that can substantially block the flow of blood into an aneurysm, such as a cerebral aneurysm, with a decreased risk of inadvertent aneurysm rupture or blood vessel wall damage. In addition, what has been needed are methods and devices suitable for blocking blood flow in cerebral aneurysms over an extended period of time without a significant risk of deformation, compaction or dislocation.

Intrasaccular occlusive devices are part of a newer type of occlusion device used to treat various intravascular conditions including aneurysms. They are often more effective at treating these wide neck conditions, or larger treatment areas. The intrasaccular devices comprise a structure which sits within the aneurysm and provides an occlusive effect at the neck of the aneurysm to help limit blood flow into the aneurysm. The rest of the device comprises a relatively conformable structure that sits within the aneurysm helping to occlude all or a portion of the aneurysm. Intrasaccular devices typically conform to the shape of the treatment site. These devices also occlude the cross section of the neck of the treatment site/aneurysm, thereby promoting clotting and causing thrombosis and closing of the aneurysm over time.

These intrasaccular devices are difficult to design for various reasons. For neurovascular aneurysms, these intrasaccular devices are particularly small and any projecting structures from the intrasaccular device can prod into the vessel or tissue, causing additional complications. In larger aneurysms, there is a risk of compaction where the intrasaccular device can migrate into the aneurysm and leave the neck region. There is a need for an intrasaccular device that addresses these issues.

SUMMARY

An intrasaccular occlusion device is described that is used to treat a variety of conditions, including aneurysms and neurovascular aneurysms. Generally, effective intrasaccular devices should provide good flow disruption at the neck of the aneurysm to reduce blood flow into the aneurysm, and should also resist migration or displacement from the treatment site in order to properly treat the aneurysm. One way to increase flow disruption at the neck region is to increase surface coverage of the material at the neck of the aneurysm. One way to prevent the issue of potential migration is to increase stiffness at the proximal part of the intrasaccular device. The following embodiments utilize various techniques to augment flow disruption and resist migration.

In one embodiment, a multiple layer occlusion device is described. A first layer comprises an entire length of the occlusion device and a second layer comprises only a proximal section of the occlusion device. The second layer helps to augment the flow-disruption effect along the proximal section of the device and provides enhanced proximal anchoring to resist migration.

In another embodiment, a multiple layer occlusion device is described. A first layer comprises an entire length of the occlusion device and a second layer comprises only a proximal section of the occlusion device so as to augment the flow-disruption effect along the proximal section of the device. In one embodiment, the second layer is free-floating or loosely attached to the first layer of the device, such that the second layer has a variable height so as to customize the portion of the occlusion device having the augmented flow-disruptive and/or occlusive effect.

In another embodiment, a multiple layer occlusion device is described. A first layer comprises an entire length of the occlusion device and a second layer comprises only a proximal section of the occlusion device so as to augment the flow-disruption effect along the proximal section of the device. In one embodiment, the second layer is a secondary mesh.

In one embodiment, a multiple layer occlusion device utilizes a relatively soft first layer which comprises an entire length of the device, and a relatively stiff second layer which comprises only a proximal section of the device. The second layer provides augmented rigidity and flow disruption to a proximal portion of the device, while the relatively soft first layer allows the device to conform to a geometry of the treatment site.

In another embodiment, a device for treatment of a patient's cerebral aneurysm is described. The device includes a first permeable shell including a radially constrained elongated state configured for delivery within a catheter lumen, an expanded state with a longitudinally shortened configuration relative to the radially constrained state, and a plurality of elongate filaments that are woven together to form a mesh, the expanded state having a proximal portion, a distal portion, and an interior cavity, wherein each of the plurality of filaments has a proximal end and a distal end, and wherein the proximal ends of each of the plurality of filaments are gathered by a proximal hub or marker band and the distal ends of each of the plurality of filaments are gathered by a distal hub or marker band. The device also includes a second permeable shell including a radially constrained elongated state configured for delivery within a catheter lumen, an expanded state with a longitudinally shortened configuration relative to the radially constrained state, and a plurality of elongate filaments that are woven together to form a mesh, wherein at least a portion of the second permeable shell is in contact with the proximal portion of the first permeable shell, wherein each of the plurality of filaments has a proximal end and a distal end. The proximal ends of each of the plurality of filaments of the second permeable shell are gathered in the proximal hub or marker band with the proximal ends of each of the plurality of filaments of the first permeable shell, and a length of the expanded state of the second permeable shell is smaller than a length of the expanded state of the first permeable shell.

In another embodiment, a method for treating a cerebral aneurysm having an interior cavity and a neck is described. The method includes the step of advancing an implant in a microcatheter to a region of interest in a cerebral artery, wherein the implant comprises a first permeable shell including a radially constrained elongated state configured for delivery within a lumen of the microcatheter, an expanded state with a longitudinally shortened configuration relative to the radially constrained state, and a plurality of elongate filaments that are woven together to form a mesh, the expanded state having a proximal portion, a distal portion, and an interior cavity, wherein each of the plurality of filaments has a proximal end and a distal end, and wherein the proximal ends of each of the plurality of filaments are gathered by a proximal hub or marker band and the distal ends of each of the plurality of filaments are gathered by a distal hub or marker band; and a second permeable shell including a radially constrained elongated state configured for delivery within the lumen of the microcatheter, an expanded state with a longitudinally shortened configuration relative to the radially constrained state, and a plurality of elongate filaments that are woven together to form a mesh, wherein at least a portion of the second permeable shell is in contact with the proximal portion of the first permeable shell, wherein each of the plurality of filaments has a proximal end and a distal end. The proximal ends of each of the plurality of filaments of the second permeable shell are gathered in the proximal hub or marker band with the proximal ends of each of the plurality of filaments of the first permeable shell, and a length of the expanded state of the second permeable shell is smaller than a length of the expanded state of the first permeable shell. The implant is then deployed within the cerebral aneurysm, wherein the first and second permeable shells each expand to their expanded states in the interior cavity of the aneurysm. The microcatheter is then withdrawn from the region of interest after deploying the implant.

In another embodiment, a device for treatment of a patient's cerebral aneurysm is described. The device includes a first self-expanding mesh including a radially constrained elongated state configured for delivery within a catheter lumen, an expanded state with a longitudinally shortened configuration relative to the radially constrained state, and a plurality of elongate filaments that are woven together to form the mesh, the expanded state having a proximal portion, a distal portion, and an interior cavity, wherein each of the plurality of filaments has a proximal end and a distal end, and wherein the proximal ends of each of the plurality of filaments are gathered by a proximal hub or marker band and the distal ends of each of the plurality of filaments are gathered by a distal hub or marker band; and a second self-expanding mesh including a radially constrained elongated state configured for delivery within a catheter lumen, an expanded state with a longitudinally shortened configuration relative to the radially constrained state, and a plurality of elongate filaments that are woven together to form the mesh, wherein at least a portion of the second self-expanding mesh is in contact with the proximal portion of the first self-expanding mesh, wherein each of the plurality of filaments has a proximal end and a distal end. The proximal ends of each of the plurality of filaments of the second self-expanding mesh are gathered in the proximal hub or marker band with the proximal ends of each of the plurality of filaments of the first self-expanding mesh, and a length of the expanded state of the second self-expanding mesh is smaller than a length of the expanded state of the first self-expanding mesh.

In another embodiment, a method for treating a cerebral aneurysm having an interior cavity and a neck is described. The method includes the step of advancing an implant in a microcatheter to a region of interest in a cerebral artery, wherein the implant comprises a first self-expanding mesh including a radially constrained elongated state configured for delivery within a catheter lumen, an expanded state with a longitudinally shortened configuration relative to the radially constrained state, and a plurality of elongate filaments that are woven together to form the mesh, the expanded state having a proximal portion, a distal portion, and an interior cavity, wherein each of the plurality of filaments has a proximal end and a distal end, and wherein the proximal ends of each of the plurality of filaments are gathered by a proximal hub or marker band and the distal ends of each of the plurality of filaments are gathered by a distal hub or marker band; and a second self-expanding mesh including a radially constrained elongated state configured for delivery within a catheter lumen, an expanded state with a longitudinally shortened configuration relative to the radially constrained state, and a plurality of elongate filaments that are woven together to form the mesh, wherein at least a portion of the second self-expanding mesh is in contact with the proximal portion of the first self-expanding mesh, wherein each of the plurality of filaments has a proximal end and a distal end. The proximal ends of each of the plurality of filaments of the second self-expanding mesh may be gathered in the proximal hub or marker band with the proximal ends of each of the plurality of filaments of the first self-expanding mesh, and a length of the expanded state of the second self-expanding mesh may be smaller than a length of the expanded state of the first self-expanding mesh. The implant is then deployed within the cerebral aneurysm, wherein the first and second self-expanding permeable meshes expand to each of their expanded states in the interior cavity of the aneurysm. The microcatheter is then withdrawn from the region of interest after deploying the implant.

In another embodiment, a device for treatment of a patient's cerebral aneurysm is described. The device includes a first permeable shell including a radially constrained elongated state configured for delivery within a catheter lumen, an expanded state with a longitudinally shortened configuration relative to the radially constrained state, and a plurality of elongate filaments that are woven together to form a mesh, the expanded state having a proximal portion, a distal portion, and an interior cavity, wherein each of the plurality of filaments has a proximal end and a distal end, and wherein the proximal ends of each of the plurality of filaments are gathered by a proximal hub or marker band and the distal ends of each of the plurality of filaments are gathered by a distal hub or marker band; and a second permeable shell including a radially constrained elongated state configured for delivery within a catheter lumen, an expanded state with a longitudinally shortened configuration relative to the radially constrained state, and a plurality of elongate filaments that are woven together to form a mesh, wherein at least a portion of the second permeable shell is in contact with the proximal portion of the first permeable shell, wherein each of the plurality of filaments has a proximal end and a distal end. The second permeable shell may have an open distal end, and a length of the expanded state of the second permeable shell may be smaller than a length of the expanded state of the first permeable shell.

In another embodiment, a method for treating a cerebral aneurysm having an interior cavity and a neck is described. The method includes the step of advancing an implant in a microcatheter to a region of interest in a cerebral artery, wherein the implant comprises a first permeable shell including a radially constrained elongated state configured for delivery within a catheter lumen, an expanded state with a longitudinally shortened configuration relative to the radially constrained state, and a plurality of elongate filaments that are woven together to form a mesh, the expanded state having a proximal portion, a distal portion, and an interior cavity, wherein each of the plurality of filaments has a proximal end and a distal end, and wherein the proximal ends of each of the plurality of filaments are gathered by a proximal hub or marker band and the distal ends of each of the plurality of filaments are gathered by a distal hub or marker band; and a second permeable shell including a radially constrained elongated state configured for delivery within a catheter lumen, an expanded state with a longitudinally shortened configuration relative to the radially constrained state, and a plurality of elongate filaments that are woven together to form a mesh, wherein at least a portion of the second permeable shell is in contact with the proximal portion of the first permeable shell, wherein each of the plurality of filaments has a proximal end and a distal end. The second permeable shell may have an open distal end, and a length of the expanded state of the second permeable shell may be smaller than a length of the expanded state of the first permeable shell. The implant is then deployed within the cerebral aneurysm, wherein the first and second permeable shells each expand to their expanded states in the interior cavity of the aneurysm. The microcatheter is then withdrawn from the region of interest after deploying the implant.

In any of the embodiments, the second permeable shell may be stiffer than the first permeable shell. The second permeable shell may have a radial stiffness or a normalized radial stiffness of between about 0.005 N/mm and about 0.025 N/mm, alternatively between about 0.010 N/mm and about 0.020 N/mm. The first permeable shell may have a normalized radial stiffness of between about 0.001 N/mm and about 0.025 N/mm, alternatively between about 0.001 N/mm and about 0.010 N/mm.

In any of the embodiments, the first permeable shell may have a soft distal portion that is deformable such that upon deployment in an aneurysm, the soft distal portion can buckle, deform, or bend. Thus, an implant having an expanded length when unconstrained and deployed outside of an aneurysm that is larger than a height of the aneurysm can still be deployed into and fit in the cavity of the aneurysm because the soft distal portion can deform, thereby reducing the effective expanded length of the device in the aneurysm.

In any of the embodiments, the second permeable shell or self-expanding mesh may be on the inside or the outside of the proximal section of the first permeable shell. Thus, an outer surface of the second permeable shell may be in contact with an inner surface of the first permeable shell. Alternatively, an outer surface of the first permeable shell may be in contact with an inner surface of the second permeable shell. The first permeable shell may be in an interior cavity defined by the second permeable shell. Alternatively, the second permeable shell may be in an interior cavity defined by the first permeable shell. The second permeable shell may have an open distal end. The proximal ends of each of the plurality of filaments of the second permeable shell are gathered in the proximal hub or marker band with the proximal ends of each of the plurality of filaments of the first permeable shell. The distal ends of each of the plurality of filaments of the second permeable shell may not attached to the first permeable shell. The distal ends of each of the plurality of filaments of the second permeable shell may also not be gathered or bound together.

In any of the embodiments, the expanded length of the second permeable shell or self-expanding mesh may less than the expanded length of the first permeable shell. The length of the expanded state of the second permeable shell may be about between about 10% to about 60%, alternatively between about 10% to about 50%, alternatively between about 10% to about 40% of the length of the expanded state of the first permeable shell.

In any of the embodiments, the second permeable shell or self-expanding mesh is made from a plurality of filaments each having first and second ends. The first ends of the second permeable shell may be bound by a hub or marker band. The first ends may be bound by the same hub or marker band that is binding the first ends (proximal ends) of the filaments of the first permeable shell, or they may be bound by a different hub or marker band. The second ends (distal ends) of the filaments may not be bound by a hub or marker band or otherwise gathered together, such that a second or distal end of the second permeable shell has an open configuration. The second ends of the filaments of the second permeable shell, i.e., the distal end or distal portion of the second permeable shell, may not be attached to the first permeable shell. In an alternative embodiment, the distal end or distal portion of the second permeable shell may be attached to the first permeable shell by, e.g., welding, adhesive, or mechanical ties along a distal section of the second shell 222. A diameter of each of the plurality of filaments of the second permeable shell may be larger than a diameter of each of the plurality of filaments of the first permeable shell.

BRIEF DESCRIPTION OF THE DRAWINGS

FIGS. 23-26 show a deployment sequence of a device for treatment of a patient's vasculature.

DETAILED DESCRIPTION

Figure 1:
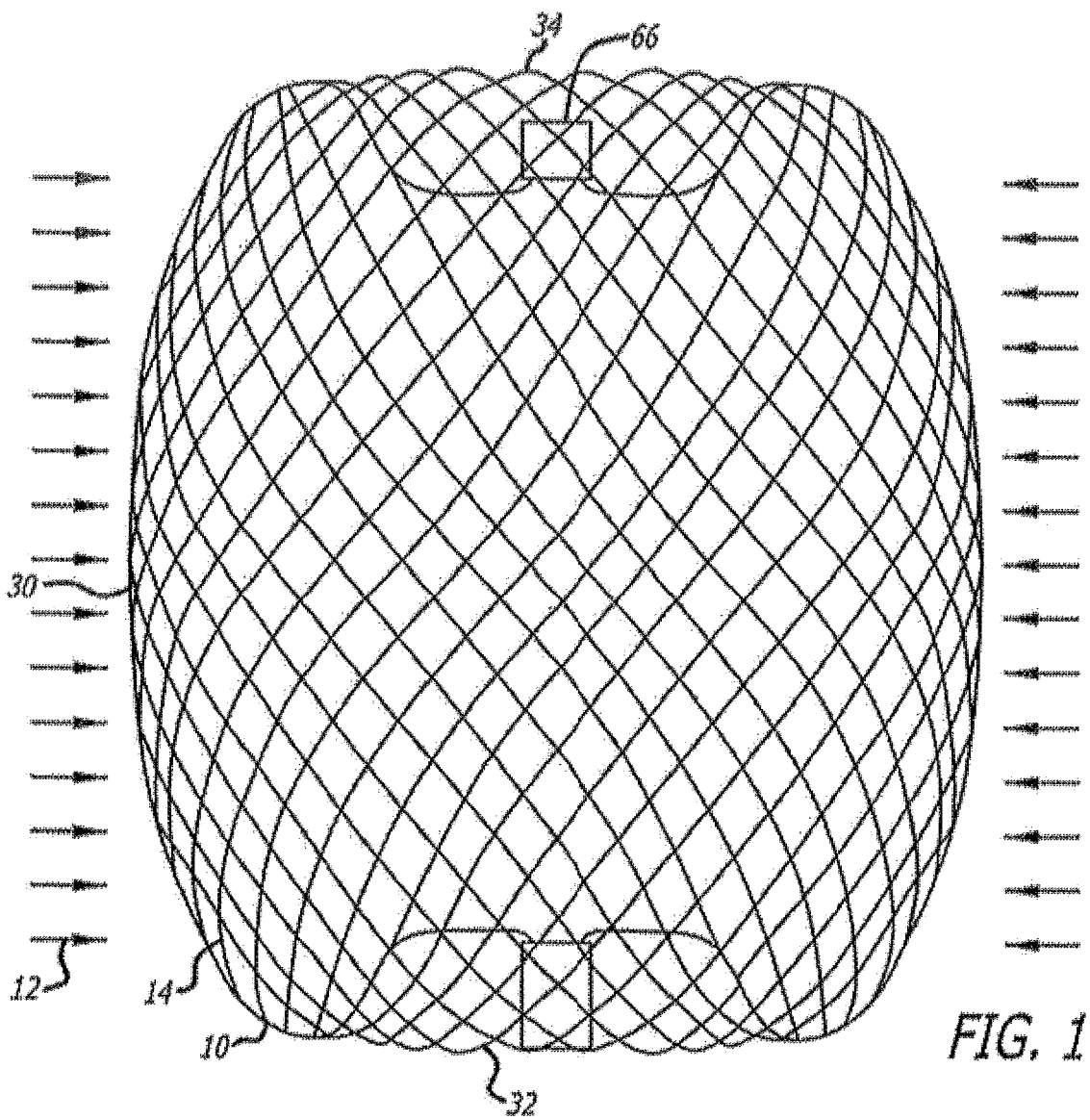
FIG. 1 is an elevation view of an embodiment of a device for treatment of a patient's vasculature and a plurality of arrows indicating inward radial force.

Discussed herein are devices and methods for the treatment of vascular defects that are suitable for minimally invasive deployment within a patient's vasculature, and particularly, within the cerebral vasculature of a patient. For such embodiments to be safely and effectively delivered to a desired treatment site and effectively deployed, some device embodiments may be configured for collapse to a low profile constrained state with a transverse dimension suitable for delivery through an inner lumen of a microcatheter and deployment from a distal end thereof. Embodiments of these devices may also maintain a clinically effective configuration with sufficient mechanical integrity once deployed so as to withstand dynamic forces within a patient's vasculature over time that may otherwise result in compaction of a deployed device. It may also be desirable for some device embodiments to acutely occlude a vascular defect of a patient during the course of a procedure in order to provide more immediate feedback regarding success of the treatment to a treating physician.

Intrasaccular occlusive devices that include a permeable shell formed from a woven or braided mesh have been described in US 2017/0095254, US 2016/0249934, US 2016/0367260, US 2016/0249937, and US 2018/0000489, all of which are hereby expressly incorporated by reference in their entirety for all purposes.

Some embodiments are particularly useful for the treatment of cerebral aneurysms by reconstructing a vascular wall so as to wholly or partially isolate a vascular defect from a patient's blood flow. Some embodiments may be configured to be deployed within a vascular defect to facilitate reconstruction, bridging of a vessel wall or both in order to treat the vascular defect. For some of these embodiments, the permeable shell of the device may be configured to anchor or fix the permeable shell in a clinically beneficial position. For some embodiments, the device may be disposed in whole or in part within the vascular defect in order to anchor or fix the device with respect to the vascular structure or defect. The permeable shell may be configured to span an opening, neck or other portion of a vascular defect in order to isolate the vascular defect, or a portion thereof, from the patient's nominal vascular system in order allow the defect to heal or to otherwise minimize the risk of the defect to the patient's health.

For some or all of the embodiments of devices for treatment of a patient's vasculature discussed herein, the permeable shell may be configured to allow some initial perfusion of blood through the permeable shell. The porosity of the permeable shell may be configured to sufficiently isolate the vascular defect so as to promote healing and isolation of the defect, but allow sufficient initial flow through the permeable shell so as to reduce or otherwise minimize the mechanical force exerted on the membrane from dynamic flow of blood or other fluids within the vasculature against the device. For some embodiments of devices for treatment of a patient's vasculature, only a portion of the permeable shell that spans the opening or neck of the vascular defect, sometimes referred to as a defect spanning portion, need be permeable and/or conducive to thrombus formation in a patient's bloodstream. For such embodiments, that portion of the device that does not span an opening or neck of the vascular defect may be substantially non-permeable or completely permeable with a pore or opening configuration that is too large to effectively promote thrombus formation.

In general, it may be desirable in some cases to use a hollow, thin walled device with a permeable shell of resilient material that may be constrained to a low profile for delivery within a patient. Such a device may also be configured to expand radially outward upon removal of the constraint such that the shell of the device assumes a larger volume and fills or otherwise occludes a vascular defect within which it is deployed. The outward radial expansion of the shell may serve to engage some or all of an inner surface of the vascular defect whereby mechanical friction between an outer surface of the permeable shell of the device and the inside surface of the vascular defect effectively anchors the device within the vascular defect. Some embodiments of such a device may also be partially or wholly mechanically captured within a cavity of a vascular defect, particularly where the defect has a narrow neck portion with a larger interior volume. In order to achieve a low profile and volume for delivery and be capable of a high ratio of expansion by volume, some device embodiments include a matrix of woven or braided filaments that are coupled together by the interwoven structure so as to form a self-expanding permeable shell having a pore or opening pattern between couplings or intersections of the filaments that is substantially regularly spaced and stable, while still allowing for conformity and volumetric constraint.

As used herein, the terms woven and braided are used interchangeably to mean any form of interlacing of filaments to form a mesh structure. In the textile and other industries, these terms may have different or more specific meanings depending on the product or application such as whether an article is made in a sheet or cylindrical form. For purposes of the present disclosure, these terms are used interchangeably.

For some embodiments, three factors may be critical for a woven or braided wire occlusion device for treatment of a patient's vasculature that can achieve a desired clinical outcome in the endovascular treatment of cerebral aneurysms. We have found that for effective use in some applications, it may be desirable for the implant device to have sufficient radial stiffness for stability, limited pore size for near-complete acute (intra-procedural) occlusion and a collapsed profile which is small enough to allow insertion through an inner lumen of a microcatheter. A device with a radial stiffness below a certain threshold may be unstable and may be at higher risk of embolization in some cases. Larger pores between filament intersections in a braided or woven structure may not generate thrombus and occlude a vascular defect in an acute setting and thus may not give a treating physician or health professional such clinical feedback that the flow disruption will lead to a complete and lasting occlusion of the vascular defect being treated. Delivery of a device for treatment of a patient's vasculature through a standard microcatheter may be highly desirable to allow access through the tortuous cerebral vasculature in the manner that a treating physician is accustomed. A detailed discussion of radial stiffness, pore size, and the necessary collapsed profile can be found in US 2017/0095254, which was previously expressly incorporated by reference in its entirety.

As has been discussed, some embodiments of devices for treatment of a patient's vasculature call for sizing the device which approximates (or with some over-sizing) the vascular site dimensions to fill the vascular site. One might assume that scaling of a device to larger dimensions and using larger filaments would suffice for such larger embodiments of a device. However, for the treatment of brain aneurysms, the diameter or profile of the radially collapsed device is limited by the catheter sizes that can be effectively navigated within the small, tortuous vessels of the brain. Further, as a device is made larger with a given or fixed number of resilient filaments having a given size or thickness, the pores or openings between junctions of the filaments are correspondingly larger. In addition, for a given filament size the flexural modulus or stiffness of the filaments and thus the structure decrease with increasing device dimension. Flexural modulus may be defined as the ratio of stress to strain. Thus, a device may be considered to have a high flexural modulus or be stiff if the strain (deflection) is low under a given force. A stiff device may also be said to have low compliance.

Figure 2:
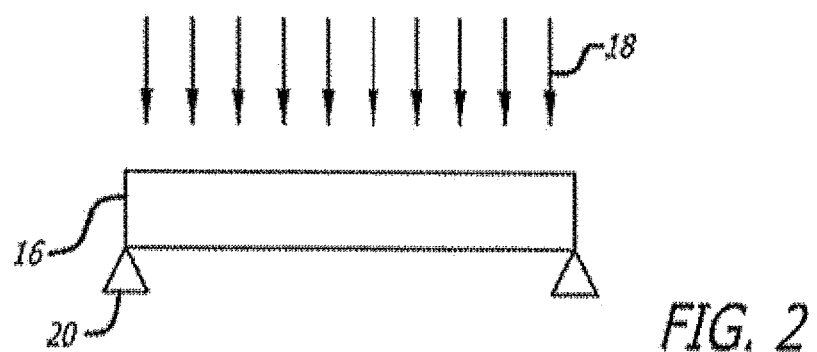
FIG. 2 is an elevation view of a beam supported by two simple supports and a plurality of arrows indicating force against the beam.
Figure 3:
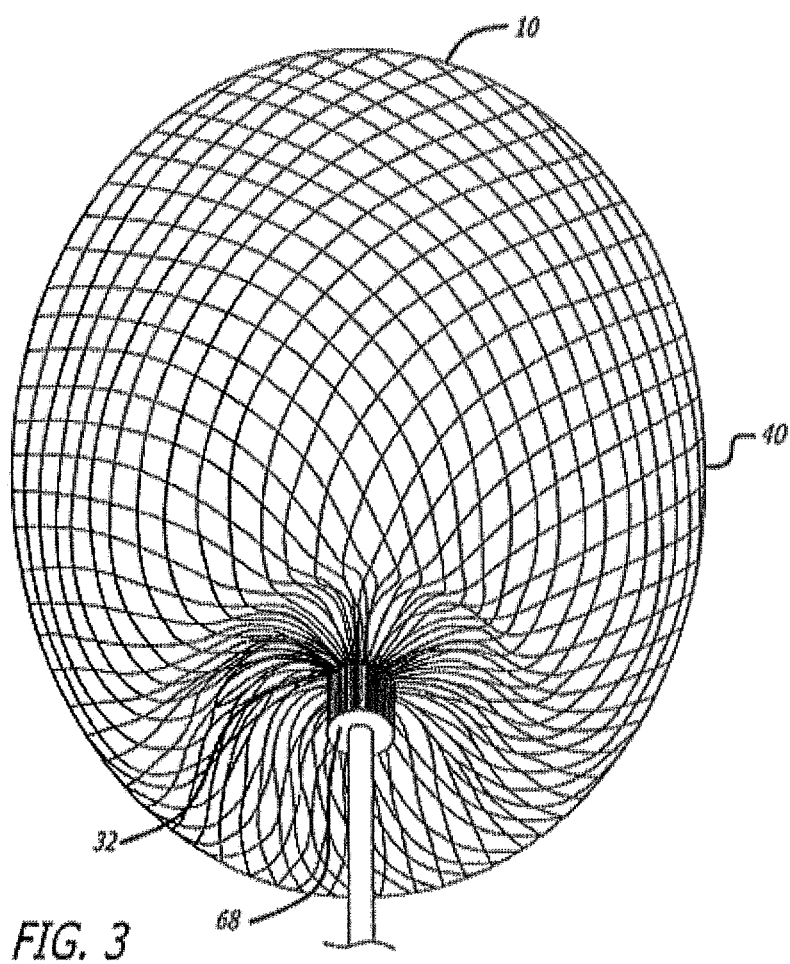
FIG. 3 is a bottom perspective view of an embodiment of a device for treatment of a patient's vasculature.

To properly configure larger size devices for treatment of a patient's vasculature, it may be useful to model the force on a device when the device is deployed into a vascular site or defect, such as a blood vessel or aneurysm, that has a diameter or transverse dimension that is smaller than a nominal diameter or transverse dimension of the device in a relaxed unconstrained state. As discussed, it may be advisable to "over-size" the device in some cases so that there is a residual force between an outside surface of the device and an inside surface of the vascular wall. The inward radial force on a device 10 that results from over-sizing is illustrated schematically in FIG. 1 with the arrows 12 in the figure representing the inward radial force. As shown in FIG. 2, these compressive forces on the filaments 14 of the device in FIG. 1 can be modeled as a simply supported beam 16 with a distributed load or force as show by the arrows 18 in the figure. It can be seen from the equation below for the deflection of a beam with two simple supports 20 and a distributed load that the deflection is a function of the length, L to the $4^{th}$ power:

Deflection of Beam=$5FL^4/384EI$ where F=force,
L=length of beam,
E=Young's Modulus, and
I=moment of inertia.

Thus, as the size of the device increases and L increases, the compliance increases substantially. Accordingly, an outward radial force exerted by an outside surface of the filaments 14 of the device 10 against a constraining force when inserted into a vascular site such as blood vessel or aneurysm is lower for a given amount of device compression or over-sizing. This force may be important in some applications to assure device stability and to reduce the risk of migration of the device and potential distal embolization.

In some embodiments, a combination of small and large filament sizes may be utilized to make a device with a desired radial compliance and yet have a collapsed profile which is configured to fit through an inner lumen of commonly used microcatheters. A device fabricated with even a small number of relatively large filaments 14 can provide reduced radial compliance (or increased stiffness) compared to a device made with all small filaments. Even a relatively small number of larger filaments may provide a substantial increase in bending stiffness due to change in the moment of Inertia that results from an increase in diameter without increasing the total cross sectional area of the filaments. The moment of inertia (I) of a round wire or filament may be defined by the equation:

$I=\pi d^4/64$ where d is the diameter of the wire or filament.

Since the moment of inertia is a function of filament diameter to the fourth power, a small change in the diameter greatly increases the moment of inertia. Thus, small changes in filament size can have substantial impact on the deflection at a given load and thus the compliance of the device.

Thus, the stiffness can be increased by a significant amount without a large increase in the cross sectional area of a collapsed profile of the device 10. This may be particularly important as device embodiments are made larger to treat large aneurysms. While large cerebral aneurysms may be relatively rare, they present an important therapeutic challenge as some embolic devices currently available to physicians have relatively poor results compared to smaller aneurysms.

As such, some embodiments of devices for treatment of a patient's vasculature may be formed using a combination of filaments 14 with a number of different diameters such as 2, 3, 4, 5 or more different diameters or transverse dimensions. In device embodiments where filaments with two different diameters are used, some larger filament embodiments may have a transverse dimension of about 0.001 inches to about 0.004 inches and some small filament embodiments may have a transverse dimension or diameter of about 0.0004 inches and about 0.0015 inches, more specifically, about 0.0004 inches to about 0.001 inches. The ratio of the number of large filaments to the number of small filaments may be between about 2 and 12 and may also be between about 4 and 8. In some embodiments, the difference in diameter or transverse dimension between the larger and smaller filaments may be less than about 0.004 inches, more specifically, less than about 0.0035 inches, and even more specifically, less than about 0.002 inches.

As discussed above, device embodiments 10 for treatment of a patient's vasculature may include a plurality of wires, fibers, threads, tubes or other filamentary elements that form a structure that serves as a permeable shell. For some embodiments, a globular shape may be formed from such filaments by connecting or securing the ends of a tubular braided structure. For such embodiments, the density of a braided or woven structure may inherently increase at or near the ends where the wires or filaments 14 are brought together and decrease at or near a middle portion 30 disposed between a proximal end 32 and distal end 34 of the permeable shell 40. For some embodiments, an end or any other suitable portion of a permeable shell 40 may be positioned in an opening or neck of a vascular defect such as an aneurysm for treatment. As such, a braided or woven filamentary device with a permeable shell may not require the addition of a separate defect spanning structure having properties different from that of a nominal portion of the permeable shell to achieve hemostasis and occlusion of the vascular defect. Such a filamentary device may be fabricated by braiding, weaving or other suitable filament fabrication techniques. Such device embodiments may be shape set into a variety of three-dimensional shapes such as discussed herein.

Referring to FIGS. 3-10, an embodiment of a device for treatment of a patient's vasculature 10 is shown. The device 10 includes a self-expanding resilient permeable shell 40 having a proximal end 32, a distal end 34, a longitudinal axis 46 and further comprising a plurality of elongate resilient filaments 14 including large filaments 48 and small filaments 50 of at least two different transverse dimensions as shown in more detail in FIGS. 5, 7, and 18. The filaments 14 have a woven structure and are secured relative to each other at proximal ends 60 and distal ends 62 thereof. The permeable shell 40 of the device has a radially constrained elongated state configured for delivery within a microcatheter 61, as shown in FIG. 11, with the thin woven filaments 14 extending longitudinally from the proximal end 42 to the distal end 44 radially adjacent each other along a length of the filaments.

As shown in FIGS. 3-6, the permeable shell 40 also has an expanded relaxed state with a globular and longitudinally shortened configuration relative to the radially constrained state. In the expanded state, the woven filaments 14 form the self-expanding resilient permeable shell 40 in a smooth path radially expanded from a longitudinal axis 46 of the device between the proximal end 32 and distal end 34. The woven structure of the filaments 14 includes a plurality of openings 64 in the permeable shell 40 formed between the woven filaments. For some embodiments, the largest of said openings 64 may be configured to allow blood flow through the openings only at a velocity below a thrombotic threshold velocity. Thrombotic threshold velocity has been defined, at least by some, as the time-average velocity at which more than 50% of a vascular graft surface is covered by thrombus when deployed within a patient's vasculature. In the context of aneurysm occlusion, a slightly different threshold may be appropriate. Accordingly, the thrombotic threshold velocity as used herein shall include the velocity at which clotting occurs within or on a device, such as device 10, deployed within a patient's vasculature such that blood flow into a vascular defect treated by the device is substantially blocked in less than about 1 hour or otherwise during the treatment procedure. The blockage of blood flow into the vascular defect may be indicated in some cases by minimal contrast agent entering the vascular defect after a sufficient amount of contrast agent has been injected into the patient's vasculature upstream of the implant site and visualized as it dissipates from that site. Such sustained blockage of flow within less than about 1 hour or during the duration of the implantation procedure may also be referred to as acute occlusion of the vascular defect.

As such, once the device 10 is deployed, any blood flowing through the permeable shell may be slowed to a velocity below the thrombotic threshold velocity and thrombus will begin to form on and around the openings in the permeable shell 40. Ultimately, this process may be configured to produce acute occlusion of the vascular defect within which the device 10 is deployed. For some embodiments, at least the distal end of the permeable shell 40 may have a reverse bend in an everted configuration such that the secured distal ends 62 of the filaments 14 are withdrawn axially within the nominal permeable shell structure or contour in the expanded state. For some embodiments, the proximal end of the permeable shell further includes a reverse bend in an everted configuration such that the secured proximal ends 60 of the filaments 14 are withdrawn axially within the nominal permeable shell structure 40 in the expanded state. As used herein, the term everted may include a structure that is everted, partially everted and/or recessed with a reverse bend as shown in the device embodiment of FIGS. 3-6. For such embodiments, the ends 60 and 62 of the filaments 14 of the permeable shell or hub structure disposed around the ends may be withdrawn within or below the globular shaped periphery of the permeable shell of the device.

The elongate resilient filaments 14 of the permeable shell 40 may be secured relative to each other at proximal ends 60 and distal ends 62 thereof by one or more methods including welding, soldering, adhesive bonding, epoxy bonding or the like. In addition to the ends of the filaments being secured together, a distal hub 66 may also be secured to the distal ends 62 of the thin filaments 14 of the permeable shell 40 and a proximal hub 68 secured to the proximal ends 60 of the thin filaments 14 of the permeable shell 40. The proximal hub 68 may include a cylindrical member that extends proximally beyond the proximal ends 60 of the thin filaments so as to form a cavity 70 within a proximal portion of the proximal hub 68. The proximal cavity 70 may be used for holding adhesives such as epoxy, solder or any other suitable bonding agent for securing an elongate detachment tether 72 that may in turn be detachably secured to a delivery apparatus such as is shown in FIG. 11.

For some embodiments, the elongate resilient filaments 14 of the permeable shell 40 may have a transverse cross section that is substantially round in shape and be made from a superelastic material that may also be a shape memory metal. The shape memory metal of the filaments of the permeable shell 40 may be heat set in the globular configuration of the relaxed expanded state as shown in FIGS. 3-6. Suitable superelastic shape memory metals may include alloys such as NiTi alloy and the like. The superelastic properties of such alloys may be useful in providing the resilient properties to the elongate filaments 14 so that they can be heat set in the globular form shown, fully constrained for delivery within an inner lumen of a microcatheter and then released to self expand back to substantially the original heat set shape of the globular configuration upon deployment within a patient's body.

The device 10 may have an everted filamentary structure with a permeable shell 40 having a proximal end 32 and a distal end 34 in an expanded relaxed state. The permeable shell 40 has a substantially enclosed configuration for the embodiments shown. Some or all of the permeable shell 40 of the device 10 may be configured to substantially block or impede fluid flow or pressure into a vascular defect or otherwise isolate the vascular defect over some period of time after the device is deployed in an expanded state. The permeable shell 40 and device 10 generally also has a low profile, radially constrained state, as shown in FIG. 11, with an elongated tubular or cylindrical configuration that includes the proximal end 32, the distal end 34 and a longitudinal axis 46. While in the radially constrained state, the elongate flexible filaments 14 of the permeable shell 40 may be disposed substantially parallel and in close lateral proximity to each other between the proximal end and distal end forming a substantially tubular or compressed cylindrical configuration.

Figure 4:
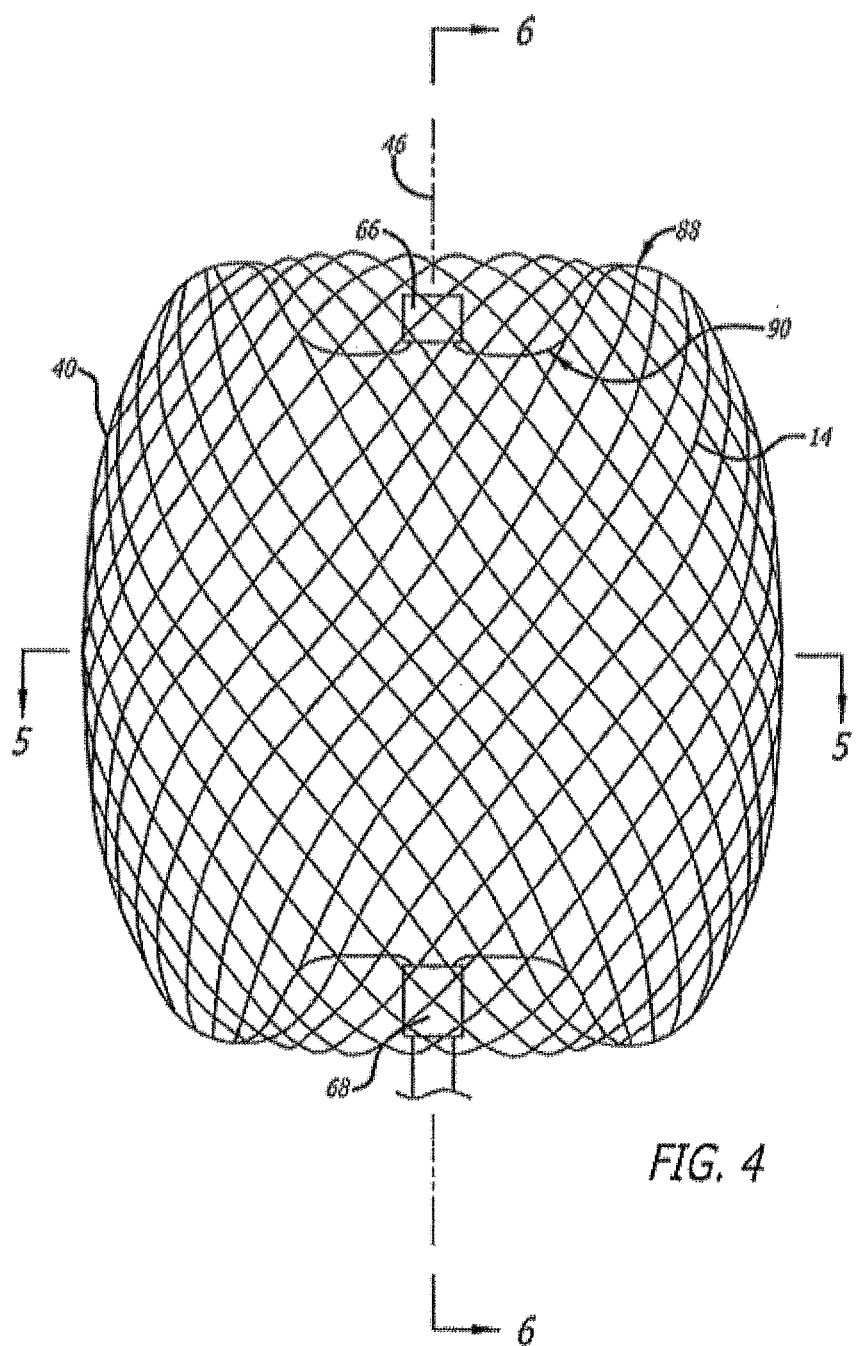
FIG. 4 is an elevation view of the device for treatment of a patient's vasculature of FIG. 3.
Figure 5:
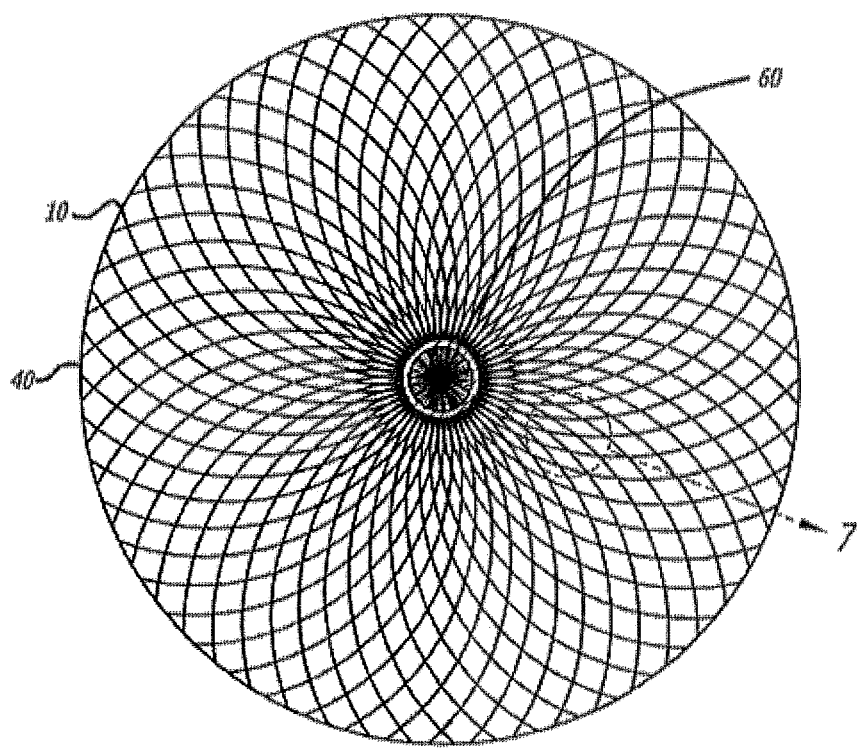
FIG. 5 is a transverse cross sectional view of the device of FIG. 4 taken along lines 5-5 in FIG. 4.

Proximal ends 60 of at least some of the filaments 14 of the permeable shell 40 may be secured to the proximal hub 68 and distal ends 62 of at least some of the filaments 14 of the permeable shell 40 are secured to the distal hub 66, with the proximal hub 68 and distal hub 66 being disposed substantially concentric to the longitudinal axis 46 as shown in FIG. 4. The ends of the filaments 14 may be secured to the respective hubs 66 and 68 by any of the methods discussed above with respect to securement of the filament ends to each other, including the use of adhesives, solder, welding and the like. A middle portion 30 of the permeable shell 40 may have a first transverse dimension with a low profile suitable for delivery from a microcatheter as shown in FIG. 11. Radial constraint on the device 10 may be applied by an inside surface of the inner lumen of a microcatheter, such as the distal end portion of the microcatheter 61 shown, or it may be applied by any other suitable mechanism that may be released in a controllable manner upon ejection of the device 10 from the distal end of the catheter. In FIG. 11 a proximal end or hub 68 of the device 10 is secured to a distal end of an elongate delivery apparatus 111 of a delivery system 112 disposed at the proximal hub 68 of the device 10. Additional details of delivery devices can be found in, e.g., US 2016/0367260, which was previously incorporated by reference in its entirety.

Some device embodiments 10 having a braided or woven filamentary structure may be formed using about 10 filaments to about 300 filaments 14, more specifically, about 10 filaments to about 100 filaments 14, and even more specifically, about 60 filaments to about 80 filaments 14. Some embodiments of a permeable shell 40 may include about 70 filaments to about 300 filaments extending from the proximal end 32 to the distal end 34, more specifically, about 100 filaments to about 200 filaments extending from the proximal end 32 to the distal end 34. For some embodiments, the filaments 14 may have a transverse dimension or diameter of about 0.0008 inches to about 0.004 inches. The elongate resilient filaments 14 in some cases may have an outer transverse dimension or diameter of about 0.0005 inch to about 0.005 inch, more specifically, about 0.001 inch to about 0.003 inch, and in some cases about 0.0004 inches to about 0.002 inches. For some device embodiments 10 that include filaments 14 of different sizes, the large filaments 48 of the permeable shell 40 may have a transverse dimension or diameter that is about 0.001 inches to about 0.004 inches and the small filaments 50 may have a transverse dimension or diameter of about 0.0004 inches to about 0.0015 inches, more specifically, about 0.0004 inches to about 0.001 inches. In addition, a difference in transverse dimension or diameter between the small filaments 50 and the large filaments 48 may be less than about 0.004 inches, more specifically, less than about 0.0035 inches, and even more specifically, less than about 0.002 inches. For embodiments of permeable shells 40 that include filaments 14 of different sizes, the number of small filaments 50 of the permeable shell 40 relative to the number of large filaments 48 of the permeable shell 40 may be about 2 to 1 to about 15 to 1, more specifically, about 2 to 1 to about 12 to 1, and even more specifically, about 4 to 1 to about 8 to 1.

The expanded relaxed state of the permeable shell 40, as shown in FIG. 4, has an axially shortened configuration relative to the constrained state such that the proximal hub 68 is disposed closer to the distal hub 66 than in the constrained state. Both hubs 66 and 68 are disposed substantially concentric to the longitudinal axis 46 of the device and each filamentary element 14 forms a smooth arc between the proximal and distal hubs 66 and 68 with a reverse bend at each end. A longitudinal spacing between the proximal and distal hubs 66 and 68 of the permeable shell 40 in a deployed relaxed state may be about 25 percent to about 75 percent of the longitudinal spacing between the proximal and distal hubs 66 and 68 in the constrained cylindrical state, for some embodiments. The arc of the filaments 14 between the proximal and distal ends 32 and 34 may be configured such that a middle portion of each filament 14 has a second transverse dimension substantially greater than the first transverse dimension.

For some embodiments, the permeable shell 40 may have a first transverse dimension in a collapsed radially constrained state of about 0.2 mm to about 2 mm and a second transverse dimension in a relaxed expanded state of about 4 mm to about 30 mm. For some embodiments, the second transverse dimension of the permeable shell 40 in an expanded state may be about 2 times to about 150 times the first transverse dimension, more specifically, about 10 times to about 25 times the first or constrained transverse dimension. A longitudinal spacing between the proximal end 32 and distal end 34 of the permeable shell 40 in the relaxed expanded state may be about 25% percent to about 75% percent of the spacing between the proximal end 32 and distal end 34 in the constrained cylindrical state. For some embodiments, a major transverse dimension of the permeable shell 40 in a relaxed expanded state may be about 4 mm to about 30 mm, more specifically, about 9 mm to about 15 mm, and even more specifically, about 4 mm to about 8 mm.

Figure 6:
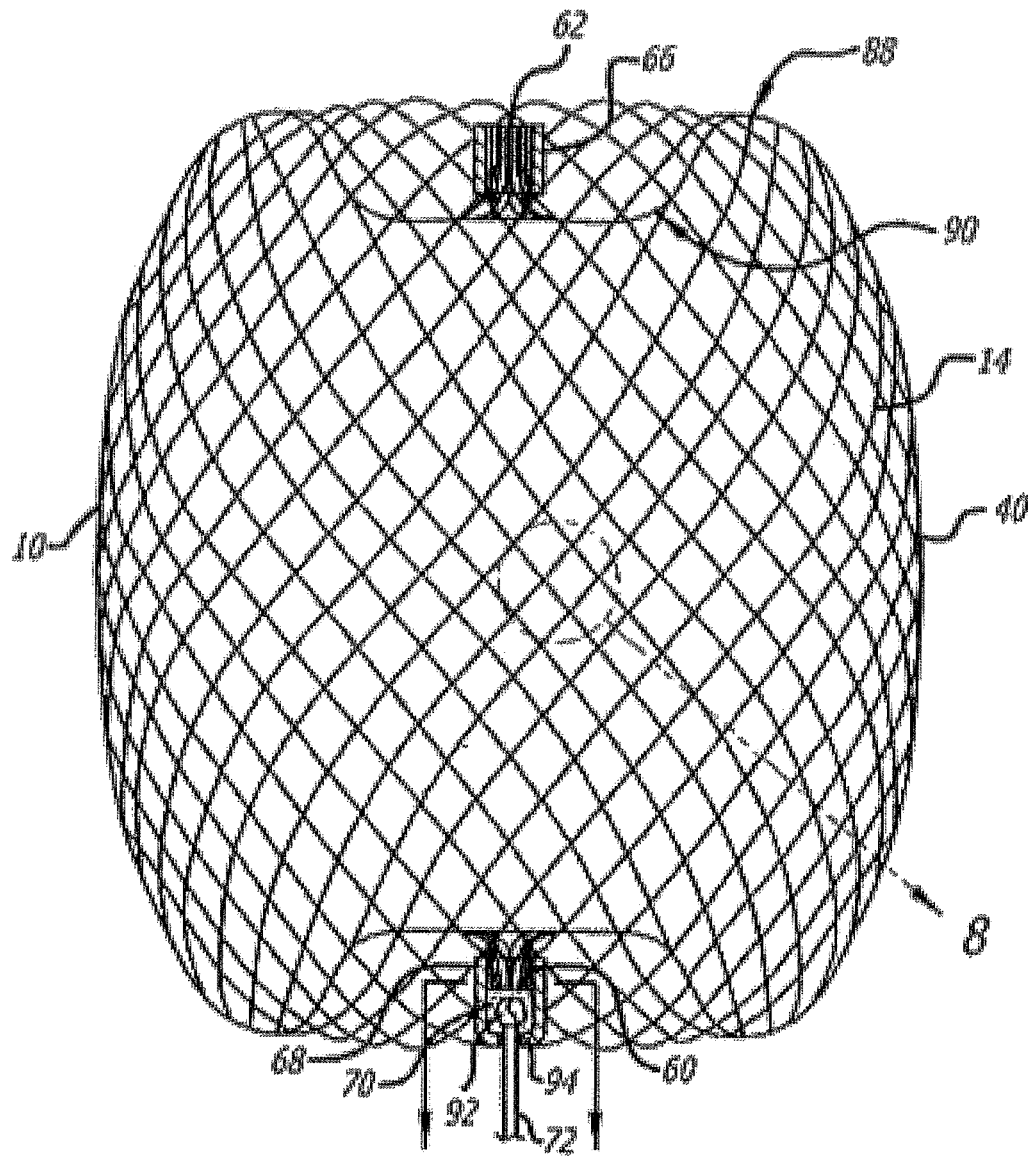
FIG. 6 shows the device of FIG. 4 in longitudinal section taken along lines 6-6 in FIG. 4.

An arced portion of the filaments 14 of the permeable shell 40 may have a sinusoidal-like shape with a first or outer radius 88 and a second or inner radius 90 near the ends of the permeable shell 40 as shown in FIG. 6. This sinusoidlike or multiple curve shape may provide a concavity in the proximal end 32 that may reduce an obstruction of flow in a parent vessel adjacent a vascular defect. For some embodiments, the first radius 88 and second radius 90 of the permeable shell 40 may be between about 0.12 mm to about 3 mm. For some embodiments, the distance between the proximal end 32 and distal end 34 may be less than about 60% of the overall length of the permeable shell 40 for some embodiments. Such a configuration may allow for the distal end 34 to flex downward toward the proximal end 32 when the device 10 meets resistance at the distal end 34 and thus may provide longitudinal conformance. The filaments 14 may be shaped in some embodiments such that there are no portions that are without curvature over a distance of more than about 2 mm. Thus, for some embodiments, each filament 14 may have a substantially continuous curvature. This substantially continuous curvature may provide smooth deployment and may reduce the risk of vessel perforation. For some embodiments, one of the ends 32 or 34 may be retracted or everted to a greater extent than the other so as to be more longitudinally or axially conformal than the other end.

The first radius 88 and second radius 90 of the permeable shell 40 may be between about 0.12 mm to about 3 mm for some embodiments. For some embodiments, the distance between the proximal end 32 and distal end 34 may be more than about 60% of the overall length of the expanded permeable shell 40. Thus, the largest longitudinal distance between the inner surfaces may be about 60% to about 90% of the longitudinal length of the outer surfaces or the overall length of device 10. A gap between the hubs 66 and 68 at the proximal end 32 and distal end 34 may allow for the distal hub 66 to flex downward toward the proximal hub 68 when the device 10 meets resistance at the distal end and thus provides longitudinal conformance. The filaments 14 may be shaped such that there are no portions that are without curvature over a distance of more than about 2 mm. Thus, for some embodiments, each filament 14 may have a substantially continuous curvature. This substantially continuous curvature may provide smooth deployment and may reduce the risk of vessel perforation. The distal end 34 may be retracted or everted to a greater extent than the proximal end 32 such that the distal end portion of the permeable shell 40 may be more radially conformal than the proximal end portion. Conformability of a distal end portion may provide better device conformance to irregular shaped aneurysms or other vascular defects. A convex surface of the device may flex inward forming a concave surface to conform to curvature of a vascular site.

Figure 10:
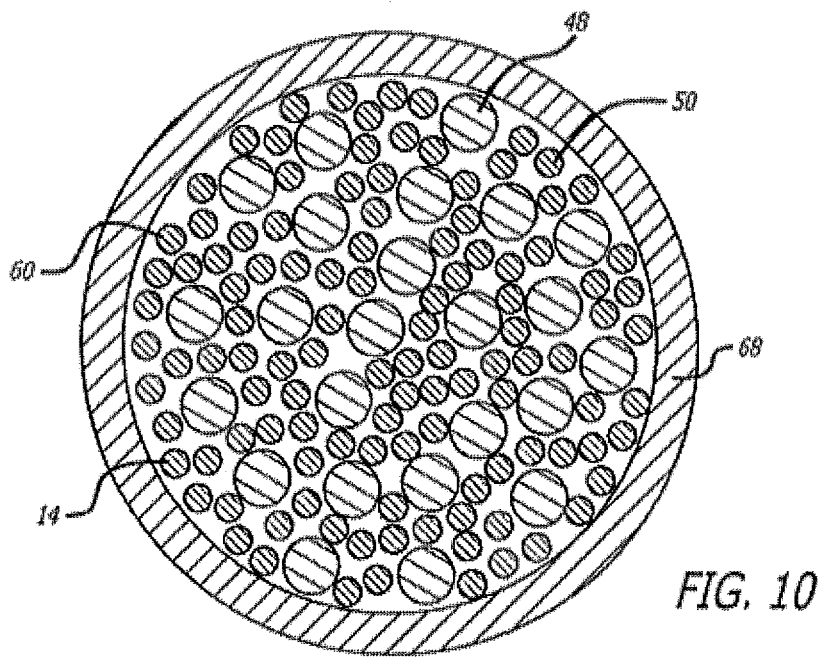
FIG. 10 is a transverse sectional view of a proximal hub portion of the device in FIG. 6 indicated by lines 10-10 in FIG. 6.
Figure 11:
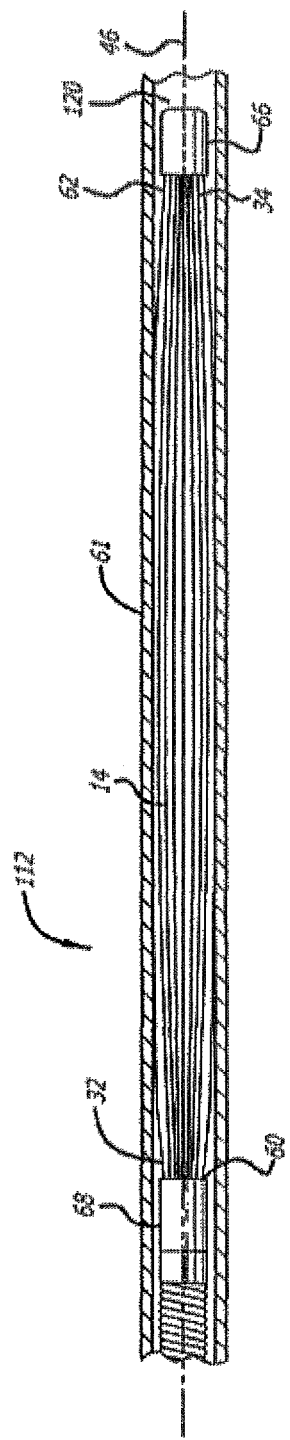
FIG. 11 is an elevation view in partial section of a distal end of a delivery catheter with the device for treatment of a patient's vasculature of FIG. 3 disposed therein in a collapsed constrained state.

FIG. 10 shows an enlarged view of the filaments 14 disposed within a proximal hub 68 of the device 10 with the filaments 14 of two different sizes constrained and tightly packed by an outer ring of the proximal hub 68. The tether member 72 may optionally be disposed within a middle portion of the filaments 14 or within the cavity 70 of the proximal hub 68 proximal of the proximal ends 60 of the filaments 14 as shown in FIG. 6. The distal end of the tether 72 may be secured with a knot 92 formed in the distal end thereof which is mechanically captured in the cavity 70 of the proximal hub 68 formed by a proximal shoulder portion 94 of the proximal hub 68. The knotted distal end 92 of the tether 72 may also be secured by bonding or potting of the distal end of the tether 72 within the cavity 70 and optionally amongst the proximal ends 60 of the filaments 14 with mechanical compression, adhesive bonding, welding, soldering, brazing or the like. The tether embodiment 72 shown in FIG. 6 has a knotted distal end 92 potted in the cavity of the proximal hub 68 with an adhesive. Such a tether 72 may be a dissolvable, severable or releasable tether that may be part of a delivery apparatus 111 used to deploy the device 10 as shown in FIG. 11 and FIGS. 23-26. FIG. 10 also shows the large filaments 48 and small filaments 50 disposed within and constrained by the proximal hub 68 which may be configured to secure the large and small filaments 48 and 50 in place relative to each other within the outer ring of the proximal hub 68.

Figure 7:
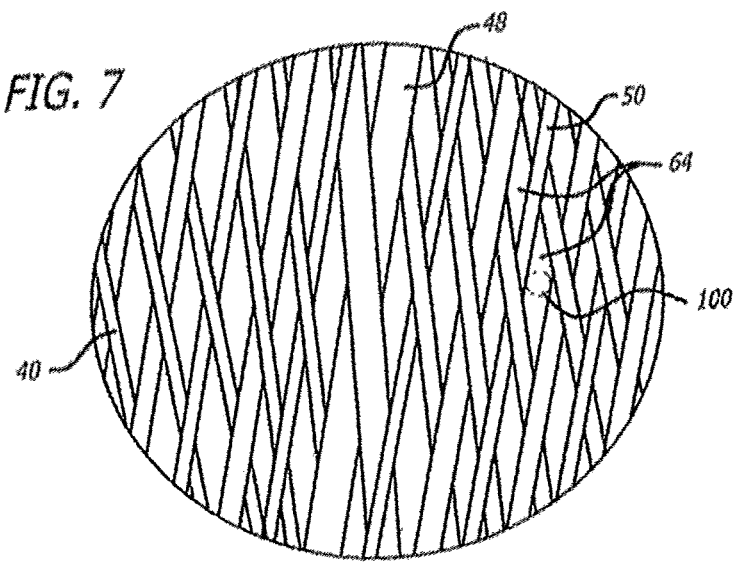
FIG. 7 is an enlarged view of the woven filament structure taken from the encircled portion 7 shown in FIG. 5.
Figure 8:
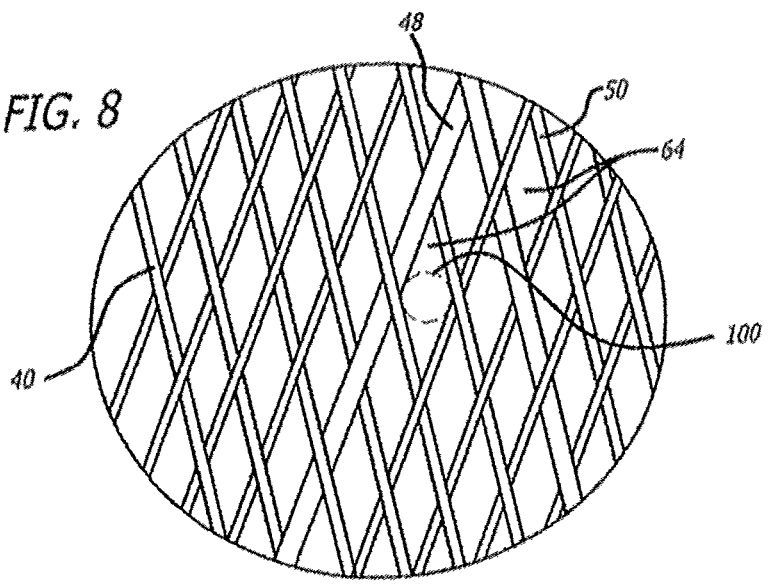
FIG. 8 is an enlarged view of the woven filament structure taken from the encircled portion 8 shown in FIG. 6.
Figure 9:
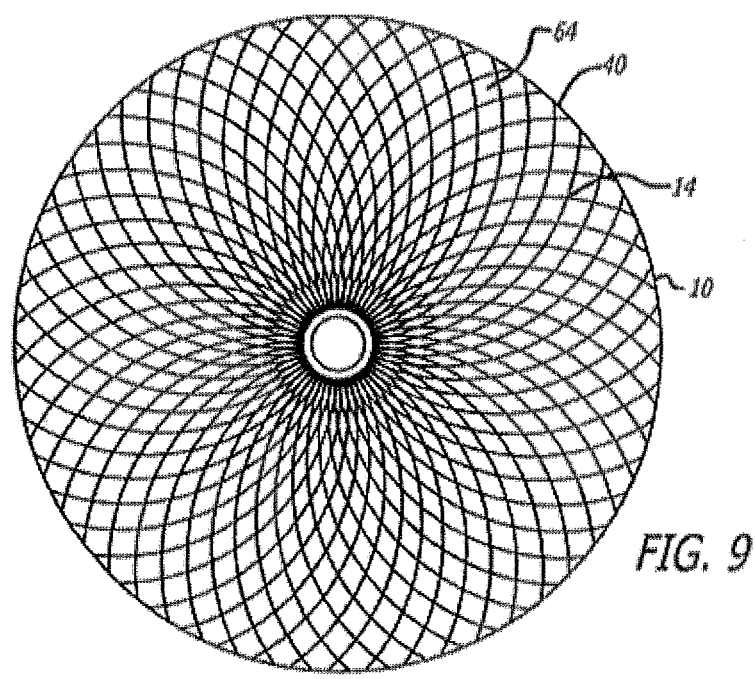
FIG. 9 is a proximal end view of the device of FIG. 3.

FIGS. 7 and 8 illustrate some configuration embodiments of braided filaments 14 of a permeable shell 40 of the device 10 for treatment of a patient's vasculature. The braid structure in each embodiment is shown with a circular shape 100 disposed within a pore 64 of a woven or braided structure with the circular shape 100 making contact with each adjacent filament segment. The pore opening size may be determined at least in part by the size of the filament elements 14 of the braid, the angle overlapping filaments make relative to each other and the picks per inch of the braid structure. For some embodiments, the cells or openings 64 may have an elongated substantially diamond shape as shown in FIG. 7, and the pores or openings 64 of the permeable shell 40 may have a substantially more square shape toward a middle portion 30 of the device 10, as shown in FIG. 8. The diamond shaped pores or openings 64 may have a length substantially greater than the width particularly near the hubs 66 and 68. In some embodiments, the ratio of diamond shaped pore or opening length to width may exceed a ratio of 3 to 1 for some cells. The diamond-shaped openings 64 may have lengths greater than the width thus having an aspect ratio, defined as Length/Width of greater than 1. The openings 64 near the hubs 66 and 68 may have substantially larger aspect ratios than those farther from the hubs as shown in FIG. 7. The aspect ratio of openings 64 adjacent the hubs may be greater than about 4 to 1. The aspect ratio of openings 64 near the largest diameter may be between about 0.75 to 1 and about 2 to 1 for some embodiments. For some embodiments, the aspect ratio of the openings 64 in the permeable shell 40 may be about 0.5 to 1 to about 2 to 1.

The pore size defined by the largest circular shapes 100 that may be disposed within openings 64 of the braided structure of the permeable shell 40 without displacing or distorting the filaments 14 surrounding the opening 64 may range in size from about 0.005 inches to about 0.01 inches, more specifically, about 0.006 inches to about 0.009 inches, even more specifically, about 0.007 inches to about 0.008 inches for some embodiments. In addition, at least some of the openings 64 formed between adjacent filaments 14 of the permeable shell 40 of the device 10 may be configured to allow blood flow through the openings 64 only at a velocity below a thrombotic threshold velocity. For some embodiments, the largest openings 64 in the permeable shell structure 40 may be configured to allow blood flow through the openings 64 only at a velocity below a thrombotic threshold velocity. As discussed above, the pore size may be less than about 0.016 inches, more specifically, less than about 0.012 inches for some embodiments. For some embodiments, the openings 64 formed between adjacent filaments 14 may be about 0.005 inches to about 0.04 inches.

Figure 12:
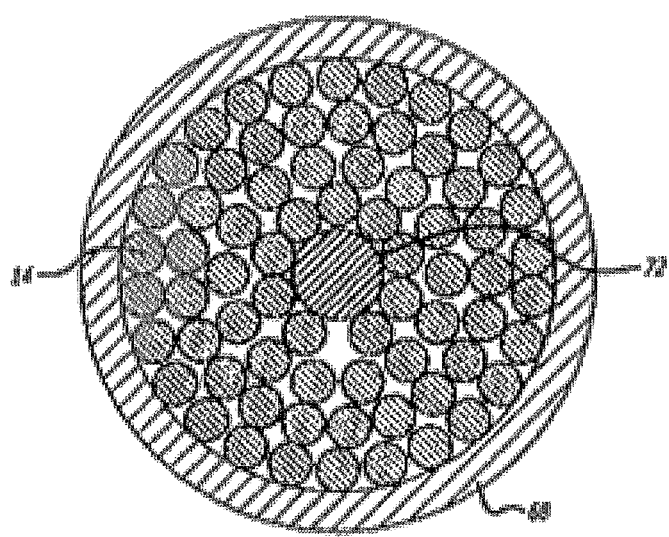
FIG. 12 illustrates an embodiment of a filament configuration for a device for treatment of a patient's vasculature.

FIG. 12 illustrates in transverse cross section an embodiment of a proximal hub 68 showing the configuration of filaments which may be tightly packed and radially constrained by an inside surface of the proximal hub 68. In some embodiments, the braided or woven structure of the permeable shell 40 formed from such filaments 14 may be constructed using a large number of small filaments. The number of filaments 14 may be greater than 125 and may also be between about 80 filaments and about 180 filaments. As discussed above, the total number of filaments 14 for some embodiments may be about 70 filaments to about 300 filaments, more specifically, about 100 filaments to about 200 filaments. In some embodiments, the braided structure of the permeable shell 40 may be constructed with two or more sizes of filaments 14. For example, the structure may have several larger filaments that provide structural support and several smaller filaments that provide the desired pore size and density and thus flow resistance to achieve a thrombotic threshold velocity in some cases. For some embodiments, small filaments 50 of the permeable shell 40 may have a transverse dimension or diameter of about 0.0006 inches to about 0.002 inches for some embodiments and about 0.0004 inches to about 0.001 inches in other embodiments. The large filaments 48 may have a transverse dimension or diameter of about 0.0015 inches to about 0.004 inches in some embodiments and about 0.001 inches to about 0.004 inches in other embodiments. The filaments 14 may be braided in a plain weave that is one under, one over structure (shown in FIGS. 7 and 8) or a supplementary weave; more than one warp interlace with one or more than one weft. The pick count may be varied between about 25 and 200 picks per inch (PPI).

Limiting blood flow into the aneurysm, as discussed above, is important with intrasaccular devices. In particular, limiting blood flow at the neck of the aneurysm is key. Furthermore, good proximal stability is important to resist movement of the device (e.g., compaction/displacement away from the neck and into the aneurysm). The following embodiments help address these issues by offering techniques to augment proximal flow-disruption and stability of an intrasaccular device.

Figure 13:
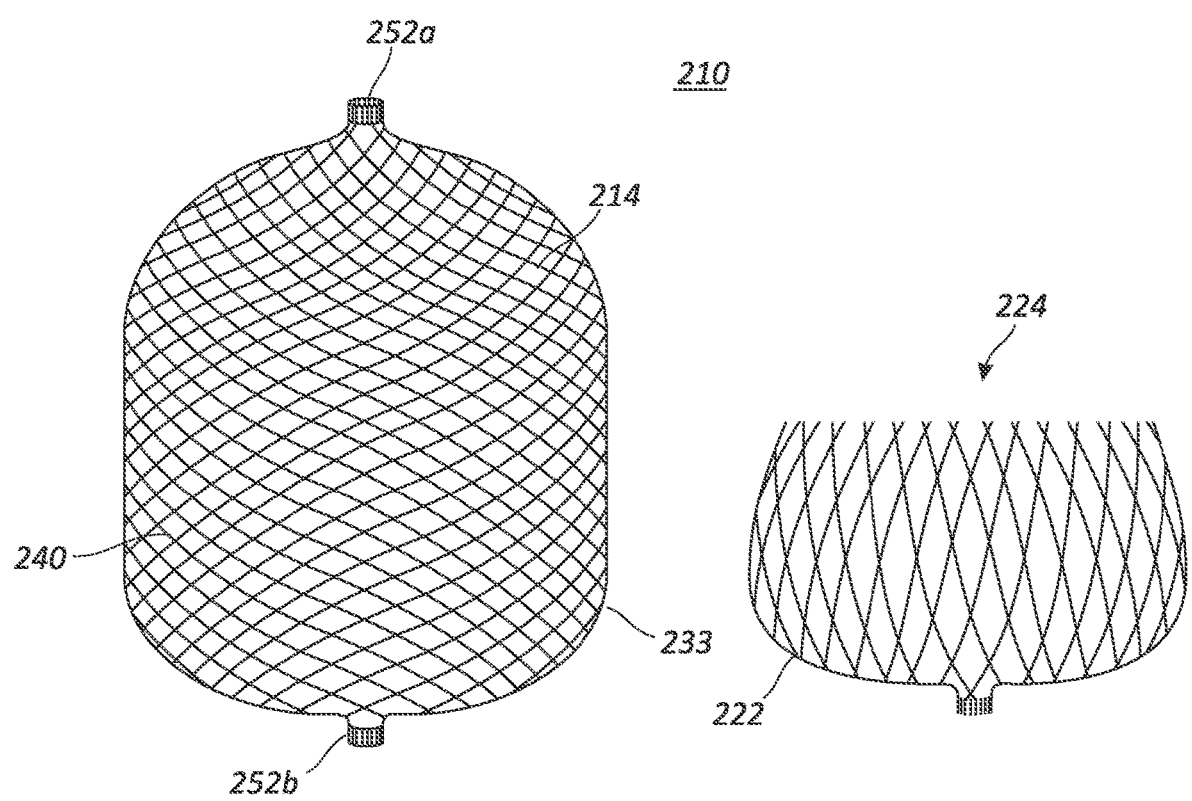
FIG. 13 illustrates the components of a multi-layer device for treatment in a patient's vasculature.
Figure 14:
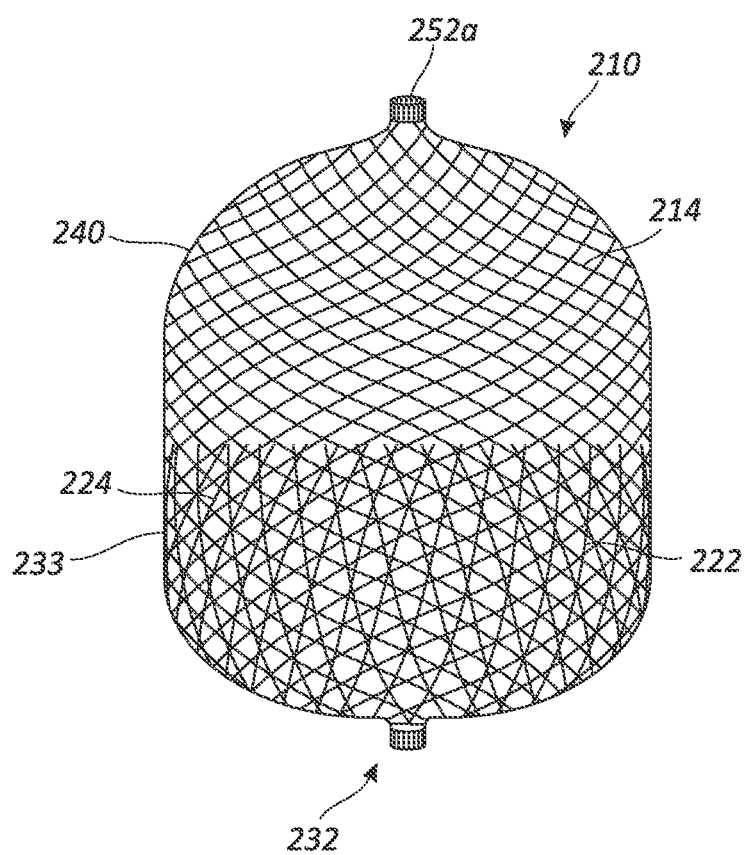
FIG. 14 illustrates a device for treatment in a patient's vasculature that has multiple layers in a proximal area of the device.
Figure 15:
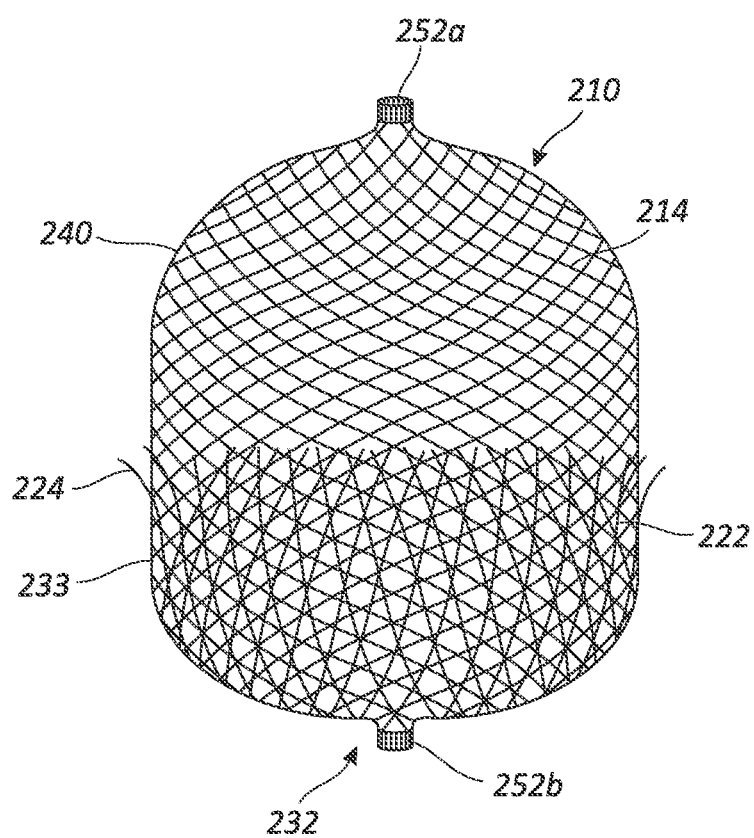
FIG. 15 illustrates an alternative device for treatment in a patient's vasculature that has multiple layers in a proximal area of the device.

FIGS. 14-15 illustrate embodiments of implantable devices 210 for treatment of a vascular defect, such as an aneurysm, that include a first shell and a second shell. FIG. 13 separately illustrates the components of the multi-layer devices 210 of FIGS. 14-15. Device 210 includes a first shell 240 spanning an entire length of the device 210, and having a radially constrained elongated state configured for delivery within a microcatheter 61, with the thin woven filaments 214 extending longitudinally from the proximal end 232 to the distal end 234 radially adjacent each other along a length of the filaments. The first shell 240 also has an expanded relaxed state with a longitudinally shortened configuration relative to the radially constrained state. In the expanded state, the woven filaments 214 form the self-expanding resilient permeable shell 240 in a smooth path radially expanded from a longitudinal axis of the device between the proximal end 232 and distal end 234.

The device further includes a second shell 222 along a proximal region of the first shell 240. The second shell 222 also has a radially constrained elongated state configured for delivery within a microcatheter 61, with the thin woven filaments 214 extending longitudinally from the proximal end 232 to a distal end 224 radially adjacent each other along a length of the filaments. The second shell 222 also has an expanded relaxed state with a longitudinally shortened configuration relative to the radially constrained state. The woven filaments 214 that form self-expanding resilient permeable shell 222 have proximal and distal ends. The proximal ends of the filaments 214 are gathered at a proximal end of the device to form a closed proximal end. The distal ends of the filaments are not gathered together, such that in the expanded state, the permeable shell 222 may have the approximate shape of a bowl, hemisphere, or spherical cap. The second shell 222 is adapted to span a proximal portion 233 of the first shell 240. The second shell 222 may be placed within an inner cavity of the first shell 240 (see FIG. 14) or may be placed such that an inner surface of the second shell 222 is in contact with an outer surface of the proximal portion 233 of the first shell 240, i.e., on the outside of the proximal part of the first shell 240 (see FIG. 15).

In one embodiment, the second shell 222 and proximal section 233 of the first shell 240 may be attached together only by a proximal hub or marker band 252*b*. In one embodiment, the second shell 222 and proximal section 233 of the first shell 240 may be attached together only by a proximal hub 252*b* (sometimes configured as a tubular marker band). One advantage of a tubular marker band (e.g. made of a radiopaque material such as tantalum, gold, platinum, or palladium) is enhanced visualization of one or both ends of the device when radiographic imaging is used. In another embodiment, the first shell 240 and the second shell 222 may be separately braided or woven and then attached, for instance, by welding, adhesive, or mechanical ties along a distal section of the second shell 222. In another embodiment, these separate mechanical attachment points are supplemented with attachment at a common proximal hub or marker band 252*b*. In one embodiment, other than the proximal hub or marker band attachment junction, the rest of the second shell 222 has some freedom of movement to help propel open the first shell 240 upon deployment from a catheter. The degree of attachment can be customized depending on the desired characteristics. For instance, where relatively high freedom of movement between first and second shells 240, 222 is desirable, relatively few attachment junctions can be used. Where relatively low freedom of movement between first and second shells 240, 222 is desirable, more attachments/attachment points can be used.

In one embodiment, attachment between first shell 240 and second shell 222 is achieved via interbraiding, such that at least a portion of second shell 222 is interwoven with first shell 222, resulting in the two shells being connected.

In one embodiment, the first shell 240 and second shell 222 are formed of similar wire sizes and are wound in a similar manner such that the stiffness profiles of each shell are substantially similar. Because the second shell 222 either overlies or sits radially within the first shell 240, the proximal region of the device 210 (where the two shells overlap) will still have enhanced stiffness due to the combined forces of the two shells, and higher flow disruption properties as the wires of each shell overlap each other, augmenting the barrier to blood entry.

In one embodiment, the first shell 240 may be softer and have a more flexible configuration than the second shell 222. The first shell 240, for instance, can use relatively smaller wires and/or a denser wind pattern than the second shell 222 in order to achieve this more flexible configuration. In contrast, the second shell 222 may be stiffer than the first shell 240. This enhanced stiffness may be achieved, for instance, by use of larger sized wires that are farther apart (e.g. having a smaller pic count). The second shell 222 can also include radiopaque components, such as tantalum, to further enhance stiffness and well as to augment visualization. A good shape memory material, such as nitinol, may also be used to create the metallic mesh for the first 240 and second 222 shells. Enhanced stiffness of the second shell 222 relative to the first shell 240 may be desirable, for instance, to enhance proximal rigidity of the device to prevent displacement from the neck of the aneurysm. Furthermore, larger wires in second shell 222 can augment the flow disruption at the proximal end of device 210, as there is more material that blood will encounter as it enters the neck of the aneurysm.

The first shell 240 may be formed by weaving or braiding between about 36 and 360 filaments, alternatively between about 72 and 216 filaments, alternatively between about 96 and 144 filaments. The filaments that are woven to form the first shell 240 may have a diameter of between about 0.0003" and 0.00125", alternatively between about 0.0005" and 0.001", alternatively between about 0.0006" and 0.0009". The first shell 240 may have a radial stiffness or a normalized radial stiffness between about 0.001 N/mm and 0.020 N/mm, alternatively between about 0.001 N/mm and 0.010 N/mm, alternatively between about 0.001 N/mm and 0.005 N/mm.

The second shell 222 may be formed by weaving or braiding between about 4 and 216 filaments, alternatively between about 4 and 144 filaments, alternatively between about 4 and 36 filaments. The filaments that are woven to form the second shell 222 may have a diameter of between about 0.001" and 0.004", alternatively between about 0.001" and 0.003", alternatively between about 0.001" and 0.002". The second shell 222 may have a radial stiffness or a normalized radial stiffness between about 0.005 N/mm and 0.040 N/mm, alternatively between about 0.005 N/mm and 0.025 N/mm, alternatively between about 0.005 N/mm and 0.020 N/mm.

In one embodiment, the device 210 may include a distal hub or marker band attachment point or hub 252*a* as a junction for the distal ends of the filaments 214 of the first shell 240. The device 210 may also include a proximal hub or marker band attachment point or hub 252*b* for the proximal ends of the filaments 214 of the first shell 240 and second shell 222. The proximal hub or marker band 252*b* may then be connected, directly or indirectly, to a mechanical pusher. A severable junction may separate the pusher from the occlusive device 210, allowing for detachment of the occlusive device 210 into the treatment site.

Though FIGS. 13-16 show the hubs or marker bands or hubs 252*a*, 252*b* as extending from the ends of the device, these can be configured in various ways. For instance, a proximal and distal dimple or recess (e.g., see FIG. 6) can be utilized where the hub or marker band sits generally within a plane of the recess, as shown in FIG. 6. Alternatively, a proximal and distal recess may be used where the hub or marker band projects outwardly from the plane of the recess so as to extend distally from the plane defining the mesh itself can be utilized.

One advantage to the inclusion of second shell 222 is that the second shell provide augmented proximal rigidity to help seating at the treatment site, as discussed above. This augmented proximal force can be beneficial in a few different ways. First, it can allow for the inclusion of a relatively soft first shell 240 than would otherwise be possible without the inclusion of a second shell 222. A soft shell 240 has some advantages in that it can more readily conform to the dimensions of the treatment site (e.g., a softer shell can manipulate its shape better if its either undersized or oversized relative to the treatment site)—however a soft shell 240 also would have less strength due to its soft nature. The inclusion of a second proximal shell 222 can enhance the rigidity of the overall device, allowing for a soft shell 240 that can better adopt to the shape of the treatment site, balanced with augmented anchoring and retention strength due to the inclusion of second shell 222. Furthermore, the inclusion of a second shell 222 can also help open a relatively soft first shell 240, by providing an anchoring force element to help pull open a softer shell 240 (e.g., where the first shell 240 and second shell 222 are connected along one or more locations).

Figure 16:
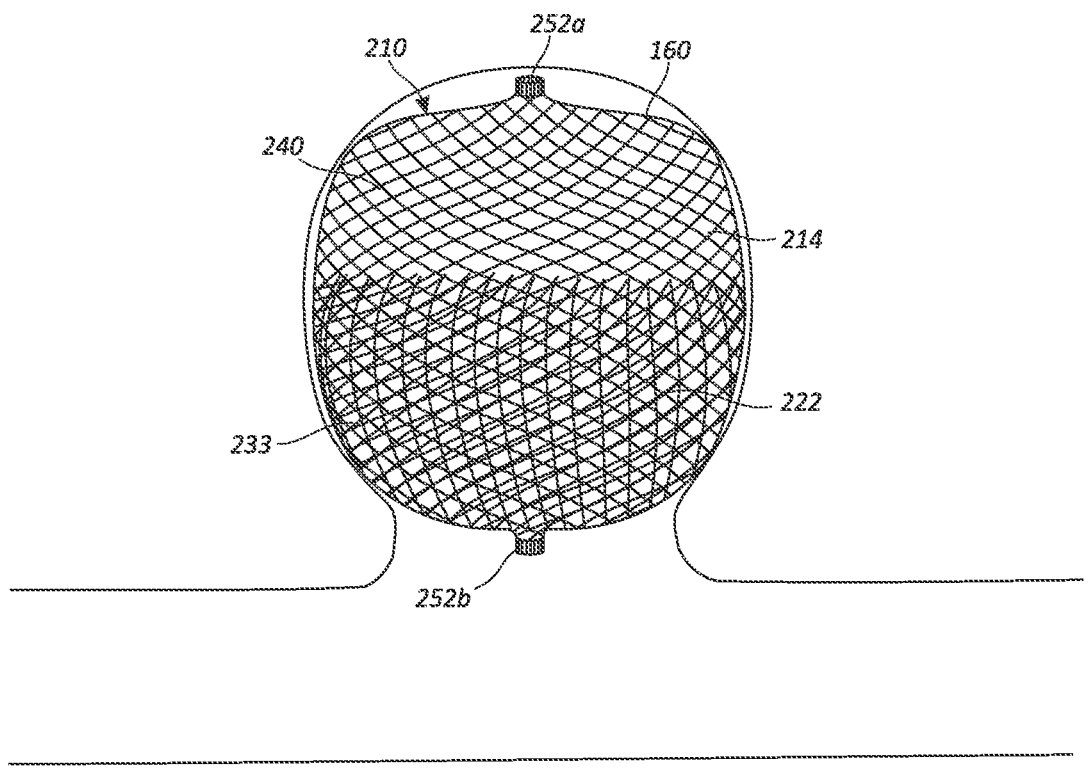
FIG. 16 illustrates a multi-layer device deployed within an aneurysm.

The device 210 can be manufactured in a number of sizes to treat different sized aneurysms. In one example, the first shell 240, and specifically the distal part of the first shell 240 is soft and able to conform to the shape of the treatment site (for instance, the dome of an aneurysm). In this way, the device 210 can be oversized relative to the treatment site, but the distal softness will allow the device 210 to deform and fold into the treatment site, thereby enhancing the overall occlusive effect of the device. Thus, the length of the expanded shape of the first shell 240 when it is not deployed in the aneurysm (i.e., unencumbered) may be larger or longer than a height of the aneurysm in which it is to be implanted. As seen in FIG. 16, the soft distal portion of the first shell 240 allows for the device 210 to buckle, deform, or fold and fit into and within the sac or interior cavity of the aneurysm. Proximal occlusion at or near the neck of the aneurysm is maximized by the use of the second shell 222, discussed above, which sits at the proximal end of the device 210 and acts as an occlusive barrier at the neck of the aneurysm/treatment site.

The expanded form of the device 210 or first shell 240 may have a longitudinal length of at least about 7 mm, alternatively at least about 8 mm, alternatively at least about 9 mm, alternatively at least about 10 mm, alternatively between about 7 mm to about 10 mm, alternatively between about 7 mm and about 9 mm. The length of the expanded form of the second shell 222 may be about 2 mm, alternatively about 3 mm, alternatively about 4 mm, alternatively between about 1.5 mm and about 4 mm, alternatively between about 2 mm and about 4 mm, alternatively between about 2 mm and about 3 mm. The length of the expanded form of the second shell 222 may be about 10%, alternatively about 20%, alternatively about 30%, alternatively about 40% of the total length of the expanded form of the first shell 240. The length of the expanded form of the second shell 222 may be between about 10% to about 40%, alternatively between about 10% to about 30%, alternatively between about 20% to about 40%, alternatively between about 25% to about 40%, alternatively between about 20% to about 30% of the total length of the expanded form of the first shell 240.

The expanded shape of device 210 can be longer than the aneurysm in which it is to be inserted, i.e., the longitudinal length of the expanded shape of the device 210 or first shell 240 can be longer than the length or height of the aneurysm in which it is being placed. The soft first shell 240 may contain wires with small diameters, which allows the first shell 240 to easily buckle or deform as it contacts the aneurysm dome. As seen in FIG. 16, the device 210 can be placed into aneurysms that are significantly shorter than the length of the expanded device 210. An additional advantage of the adjustability of the heights of the device 210 is that a single size of device 10 can treat a range of aneurysms with different heights. For example, a device 210 with a length or height of 7 mm may be able to treat 5.5-6 mm diameter aneurysms with a range of heights as a result of the compressibility of the soft first shell 240.

For some embodiments, the permeable shell 40, 240 or portions thereof may be porous and may be highly permeable to liquids. In contrast to most vascular prosthesis fabrics or grafts which typically have a water permeability below 2,000 ml/min/cm$^2$ when measured at a pressure of 120 mmHg, the permeable shell 40 of some embodiments discussed herein may have a water permeability greater than about 2,000 ml/min/cm$^2$, in some cases greater than about 2,500 ml/min/cm$^2$. For some embodiments, water permeability of the permeable shell 40 or portions thereof may be between about 2,000 and 10,000 ml/min/cm$^2$, more specifically, about 2,000 ml/min/cm$^2$ to about 15,000 ml/min/cm$^2$, when measured at a pressure of 120 mmHg.

Device embodiments and components thereof may include metals, polymers, biologic materials and composites thereof. Suitable metals include zirconium-based alloys, cobalt-chrome alloys, nickel-titanium alloys, platinum, tantalum, stainless steel, titanium, gold, and tungsten. Potentially suitable polymers include but are not limited to acrylics, silk, silicones, polyvinyl alcohol, polypropylene, polyvinyl alcohol, polyesters (e.g. polyethylene terephthalate or PET), PolyEtherEther Ketone (PEEK), polytetrafluoroethylene (PTFE), polycarbonate urethane (PCU) and polyurethane (PU). Device embodiments may include a material that degrades or is absorbed or eroded by the body. A bioresorbable (e.g., breaks down and is absorbed by a cell, tissue, or other mechanism within the body) or bioabsorbable (similar to bioresorbable) material may be used. Alternatively, a bioerodable (e.g., erodes or degrades over time by contact with surrounding tissue fluids, through cellular activity or other physiological degradation mechanisms), biodegradable (e.g., degrades over time by enzymatic or hydrolytic action, or other mechanism in the body), or dissolvable material may be employed. Each of these terms is interpreted to be interchangeable. bioabsorbable polymer. Potentially suitable bioabsorbable materials include polylactic acid (PLA), poly(alpha-hydroxy acid) such as poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(amino acids), or related copolymer materials. An absorbable composite fiber may be made by combining a reinforcement fiber made from a copolymer of about 18% glycolic acid and about 82% lactic acid with a matrix material consisting of a blend of the above copolymer with about 20% polycaprolactone (PCL).

Permeable shell embodiments 40, 240 may be formed at least in part of wire, ribbon, or other filamentary elements 14, 214. These filamentary elements 14 may have circular, elliptical, ovoid, square, rectangular, or triangular crosssections. Permeable shell embodiments 40 may also be formed using conventional machining, laser cutting, electrical discharge machining (EDM) or photochemical machining (PCM). If made of a metal, it may be formed from either metallic tubes or sheet material.

Figure 17:
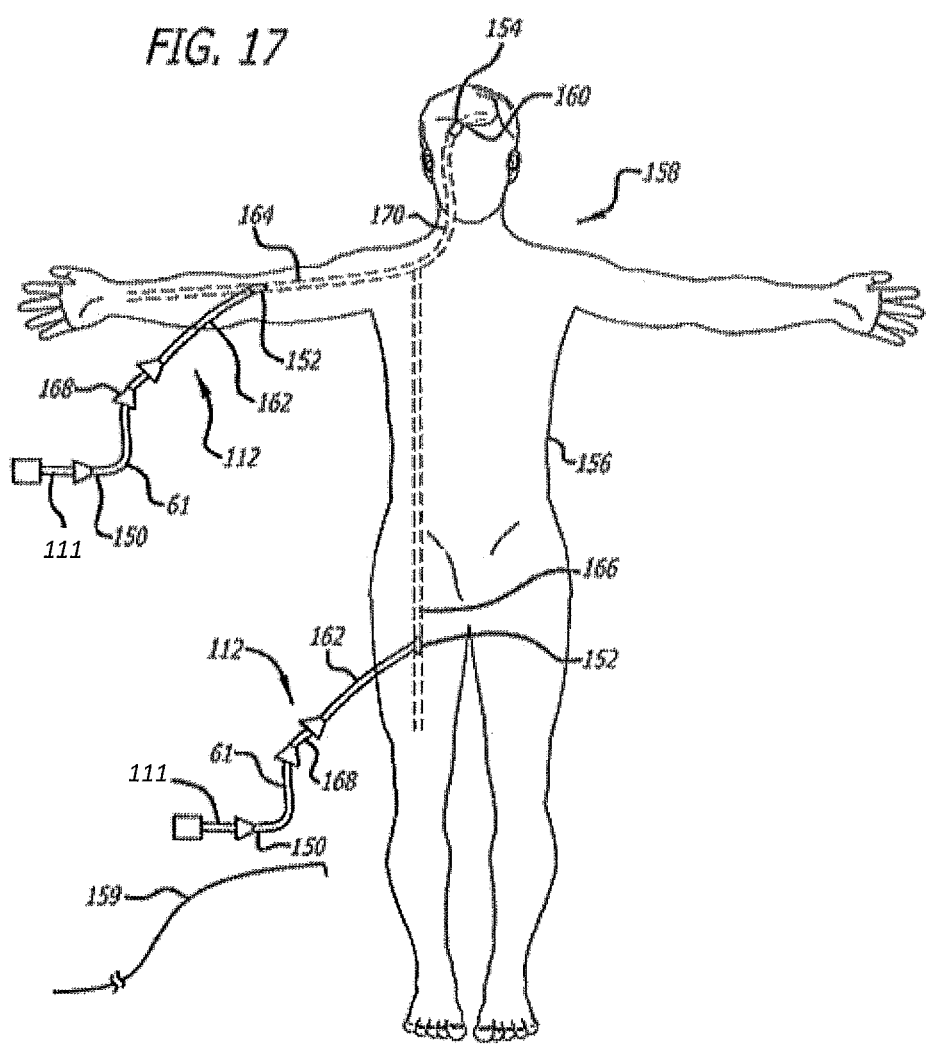
FIG. 17 is a schematic view of a patient being accessed by an introducer sheath, a microcatheter and a device for treatment of a patient's vasculature releasably secured to a distal end of a delivery device or actuator.
Figure 18:
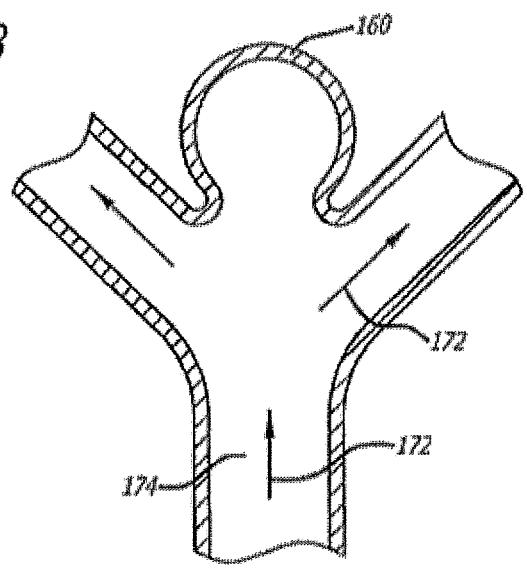
FIG. 18 is a sectional view of a terminal aneurysm.

Device embodiments 10, 210 discussed herein may be delivered and deployed from a delivery and positioning system 112 that includes a microcatheter 61, such as the type of microcatheter 61 that is known in the art of neurovascular navigation and therapy. Device embodiments for treatment of a patient's vasculature 10, 210 may be elastically collapsed and restrained by a tube or other radial restraint, such as an inner lumen 120 of a microcatheter 61, for delivery and deployment. The microcatheter 61 may generally be inserted through a small incision 152 accessing a peripheral blood vessel such as the femoral artery or brachial artery. The microcatheter 61 may be delivered or otherwise navigated to a desired treatment site 154 from a position outside the patient's body 156 over a guidewire 159 under fluoroscopy or by other suitable guiding methods. The guidewire 159 may be removed during such a procedure to allow insertion of the device 10, 210 secured to a delivery apparatus 111 of the delivery system 112 through the inner lumen 120 of a microcatheter 61 in some cases. FIG. 17 illustrates a schematic view of a patient 158 undergoing treatment of a vascular defect 160 as shown in FIG. 18. An access sheath 162 is shown disposed within either a radial artery 164 or femoral artery 166 of the patient 158 with a delivery system 112 that includes a microcatheter 61 and delivery apparatus 111 disposed within the access sheath 162. The delivery system 112 is shown extending distally into the vasculature of the patient's brain adjacent a vascular defect 160 in the patient's brain.

Access to a variety of blood vessels of a patient may be established, including arteries such as the femoral artery 166, radial artery 164, and the like in order to achieve percutaneous access to a vascular defect 160. In general, the patient 158 may be prepared for surgery and the access artery is exposed via a small surgical incision 152 and access to the lumen is gained using the Seldinger technique where an introducing needle is used to place a wire over which a dilator or series of dilators dilates a vessel allowing an introducer sheath 162 to be inserted into the vessel. This would allow the device to be used percutaneously. With an introducer sheath 162 in place, a guiding catheter 168 is then used to provide a safe passageway from the entry site to a region near the target site 154 to be treated. For example, in treating a site in the human brain, a guiding catheter 168 would be chosen which would extend from the entry site 152 at the femoral artery up through the large arteries extending around the heart through the aortic arch, and downstream through one of the arteries extending from the upper side of the aorta such as the carotid artery 170. Typically, a guidewire 159 and neurovascular microcatheter 61 are then placed through the guiding catheter 168 and advanced through the patient's vasculature, until a distal end 151 of the microcatheter 61 is disposed adjacent or within the target vascular defect 160, such as an aneurysm. Exemplary guidewires 159 for neurovascular use include the Synchro2® made by Boston Scientific and the Glidewire Gold Neuro® made by MicroVention Terumo. Typical guidewire sizes may include 0.014 inches and 0.018 inches. Once the distal end 151 of the catheter 61 is positioned at the site, often by locating its distal end through the use of radiopaque marker material and fluoroscopy, the catheter is cleared. For example, if a guidewire 159 has been used to position the microcatheter 61, it is withdrawn from the catheter 61 and then the implant delivery apparatus 111 is advanced through the microcatheter 61.

Delivery and deployment of device embodiments 10, 210 discussed herein may be carried out by first compressing the device 10, 210 to a radially constrained and longitudinally flexible state as shown in FIG. 11. The device 10, 210 may then be delivered to a desired treatment site 154 while disposed within the microcatheter 61, and then ejected or otherwise deployed from a distal end 151 of the microcatheter 61. In other method embodiments, the microcatheter 61 may first be navigated to a desired treatment site 154 over a guidewire 159 or by other suitable navigation techniques. The distal end of the microcatheter 61 may be positioned such that a distal port of the microcatheter 61 is directed towards or disposed within a vascular defect 160 to be treated and the guidewire 159 withdrawn. The device 10, 210 secured to a suitable delivery apparatus 111 may then be radially constrained, inserted into a proximal portion of the inner lumen 120 of the microcatheter 61 and distally advanced to the vascular defect 160 through the inner lumen 120.

Once disposed within the vascular defect 160, the device 10, 210 may then allowed to assume an expanded relaxed or partially relaxed state with the permeable shell 40, 240 of the device spanning or partially spanning a portion of the vascular defect 160 or the entire vascular defect 160. The device 10, 210 may also be activated by the application of an energy source to assume an expanded deployed configuration once ejected from the distal section of the microcatheter 61 for some embodiments. Once the device 10 is deployed at a desired treatment site 154, the microcatheter 61 may then be withdrawn.

Figure 19:
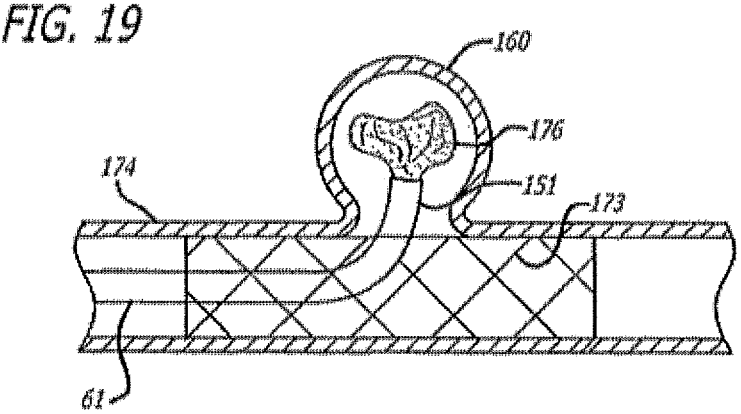
FIG. 19 is a sectional view of an aneurysm.

Some embodiments of devices for the treatment of a patient's vasculature 10, 210 discussed herein may be directed to the treatment of specific types of defects of a patient's vasculature. For example, referring to FIG. 18, an aneurysm 160 commonly referred to as a terminal aneurysm is shown in section. Terminal aneurysms occur typically at bifurcations in a patient's vasculature where blood flow, indicated by the arrows 172, from a supply vessel splits into two or more branch vessels directed away from each other. The main flow of blood from the supply vessel 174, such as a basilar artery, sometimes impinges on the vessel where the vessel diverges and where the aneurysm sack forms. Terminal aneurysms may have a well defined neck structure where the profile of the aneurysm 160 narrows adjacent the nominal vessel profile, but other terminal aneurysm embodiments may have a less defined neck structure or no neck structure. FIG. 19 illustrates a typical berry type aneurysm 160 in section where a portion of a wall of a nominal vessel section weakens and expands into a sack like structure ballooning away from the nominal vessel surface and profile. Some berry type aneurysms may have a well-defined neck structure as shown in FIG. 19, but others may have a less defined neck structure or none at all. FIG. 19 also shows some optional procedures wherein a stent 173 or other type of support has been deployed in the parent vessel 174 adjacent the aneurysm. Also, shown is embolic material 176 being deposited into the aneurysm 160 through a microcatheter 61. Either or both of the stent 173 and embolic material 176 may be so deployed either before or after the deployment of a device for treatment of a patient's vasculature 10.

Figure 28:
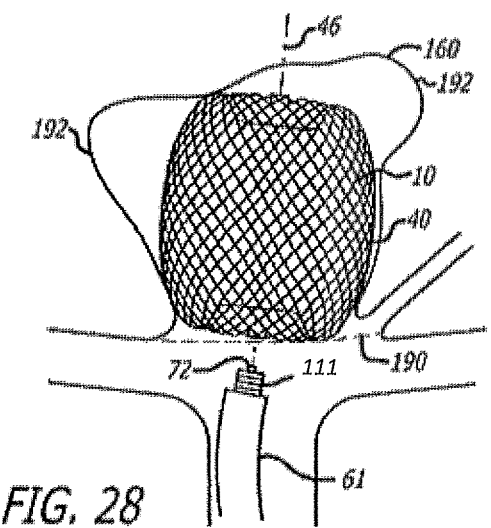
FIG. 28 is an elevation view in partial section of an embodiment of a device for treatment of a patient's vasculature deployed within an irregularly shaped aneurysm.

Prior to delivery and deployment of a device for treatment of a patient's vasculature 10, 210, it may be desirable for the treating physician to choose an appropriately sized device 10, 210 to optimize the treatment results. Some embodiments of treatment may include estimating a volume of a vascular site or defect 160 to be treated and selecting a device 10, 210 with a volume that is substantially the same volume or slightly over-sized relative to the volume of the vascular site or defect 160. The volume of the vascular defect 160 to be occluded may be determined using three-dimensional angiography or other similar imaging techniques along with software which calculates the volume of a selected region. The amount of over-sizing may be between about 2% and 15% of the measured volume. In some embodiments, such as a very irregular shaped aneurysm, it may be desirable to under-size the volume of the device 10, 210. Small lobes or "daughter aneurysms" may be excluded from the volume, defining a truncated volume which may be only partially filled by the device without affecting the outcome. A device 10, 210 deployed within such an irregularly shaped aneurysm 160 is shown in FIG. 28 discussed below. Such a method embodiment may also include implanting or deploying the device 10, 210 so that the vascular defect 160 is substantially filled volumetrically by a combination of device and blood contained therein. The device 10, 210 may be configured to be sufficiently conformal to adapt to irregular shaped vascular defects 160 so that at least about 75%, in some cases about 80%, of the vascular defect volume is occluded by a combination of device 10, 210 and blood contained therein.

Figure 20:
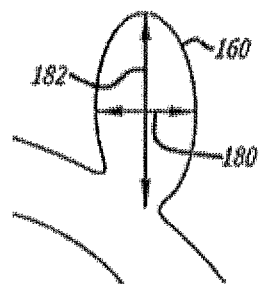
FIG. 20 is a schematic view in section of an aneurysm showing perpendicular arrows which indicate interior nominal longitudinal and transverse dimensions of the aneurysm.
Figure 21:
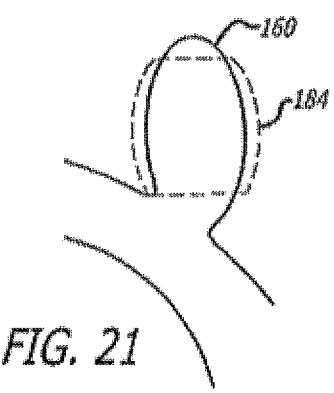
FIG. 21 is a schematic view in section of the aneurysm of FIG. 20 with a dashed outline of a device for treatment of a patient's vasculature in a relaxed unconstrained state that extends transversely outside of the walls of the aneurysm.
Figure 22:
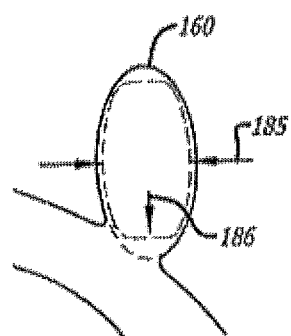
FIG. 22 is a schematic view in section of an outline of a device represented by the dashed line in FIG. 21 in a deployed and partially constrained state within the aneurysm.

In particular, for some treatment embodiments, it may be desirable to choose a device 10, 210 that is properly over-sized in a transverse dimension so as to achieve a desired conformance, radial force and fit after deployment of the device 10. FIGS. 20-22 illustrate a schematic representation of how a device 10, 210 may be chosen for a proper fit after deployment that is initially oversized in a transverse dimension by at least about 10% of the largest transverse dimension of the vascular defect 160 and sometimes up to about 100% of the largest transverse dimension. For some embodiments, the device 10, 210 may be oversized a small amount (e.g. less than about 1.5 mm) in relation to measured dimensions for the width, height or neck diameter of the vascular defect 160.

In FIG. 20, a vascular defect 160 in the form of a cerebral aneurysm is shown with horizontal arrows 180 and vertical arrows 182 indicating the approximate largest interior dimensions of the defect 160. Arrow 180 extending horizontally indicates the largest transverse dimension of the defect 160. In FIG. 21, a dashed outline 184 of a device for treatment of the vascular defect is shown superimposed over the vascular defect 160 of FIG. 20 illustrating how a device 10, 210 that has been chosen to be approximately 20% oversized in a transverse dimension would look in its unconstrained, relaxed state. FIG. 22 illustrates how the device 10, 210, which is indicated by the dashed line 184 of FIG. 21 might conform to the interior surface of the vascular defect 160 after deployment whereby the nominal transverse dimension of the device 10, 210 in a relaxed unconstrained state has now been slightly constrained by the inward radial force 185 exerted by the vascular defect 160 on the device 10, 210. In response, as the filaments 14, 214 of the device 10, 210 and thus the permeable shell 40, 240 made therefrom have a constant length, the device 10, 210 has assumed a slightly elongated shape in the axial or longitudinal axis of the device 10 so as to elongate and better fill the interior volume of the defect 160 as indicated by the downward arrow 186 in FIG. 22.

Once a properly sized device 10, 210 has been selected, the delivery and deployment process may then proceed. It should also be noted also that the properties of the device embodiments 10, 210 and delivery system embodiments 112 discussed herein generally allow for retraction of a device 10 after initial deployment into a defect 160, but before detachment of the device 10, 210. Therefore, it may also be possible and desirable to withdraw or retrieve an initially deployed device 10 after the fit within the defect 160 has been evaluated in favor of a differently sized device 10, 210. An example of a terminal aneurysm 160 is shown in FIG. 23 in section. The tip 151 of a catheter, such as a microcatheter 61 may be advanced into or adjacent the vascular site or defect 160 (e.g. aneurysm) as shown in FIG. 24. For some embodiments, an embolic coil or other vaso-occlusive device or material 176 (as shown for example in FIG. 19) may optionally be placed within the aneurysm 160 to provide a framework for receiving the device 10, 210. In addition, a stent 173 may be placed within a parent vessel 174 of some aneurysms substantially crossing the aneurysm neck prior to or during delivery of devices for treatment of a patient's vasculature discussed herein (also as shown for example in FIG. 19). An example of a suitable microcatheter 61 having an inner lumen diameter of about 0.020 inches to about 0.022 inches is the Rapid Transit® manufactured by Cordis Corporation. Examples of some suitable microcatheters 61 may include microcatheters having an inner lumen diameter of about 0.026 inch to about 0.028 inch, such as the Rebar® by Ev3 Company, the Renegade Hi-Flow® by Boston Scientific Corporation, and the Mass Transit® by Cordis Corporation. Suitable microcatheters having an inner lumen diameter of about 0.031 inch to about 0.033 inch may include the Marksmen® by Chestnut Medical Technologies, Inc. and the Vasco 28® by Balt Extrusion. A suitable microcatheter 61 having an inner lumen diameter of about 0.039 inch to about 0.041 inch includes the Vasco 35 by Balt Extrusion. These microcatheters 61 are listed as exemplary embodiments only, other suitable microcatheters may also be used with any of the embodiments discussed herein.

Detachment of the device 10, 210 from the delivery apparatus 111 may be controlled by a control switch 188 disposed at a proximal end of the delivery system 112, which may also be coupled to an energy source 142, which severs the tether 72 that secures the proximal hub 68 of the device 10 to the delivery apparatus 111. While disposed within the microcatheter 61 or other suitable delivery system 112, as shown in FIG. 11, the filaments 14, 214 of the permeable shell 40, 240 may take on an elongated, non-everted configuration substantially parallel to each other and a longitudinal axis of the catheter 61. Once the device 10, 210 is pushed out of the distal port of the microcatheter 61, or the radial constraint is otherwise removed, the distal ends 62 of the filaments 14, 214 may then axially contract towards each other so as to assume the globular everted configuration within the vascular defect 160 as shown in FIG. 25.

The device 10, 210 may be inserted through the microcatheter 61 such that the catheter lumen 120 restrains radial expansion of the device 10, 210 during delivery. Once the distal tip or deployment port of the delivery system 112 is positioned in a desirable location adjacent or within a vascular defect 160, the device 10, 210 may be deployed out the distal end of the catheter 61 thus allowing the device to begin to radially expand as shown in FIG. 25. As the device 10, 210 emerges from the distal end of the delivery system 112, the device 10, 210 expands to an expanded state within the vascular defect 160, but may be at least partially constrained by an interior surface of the vascular defect 160.

Upon full deployment, radial expansion of the device 10, 210 may serve to secure the device 10, 210 within the vascular defect 160 and also deploy the permeable shell 40 across at least a portion of an opening 190 (e.g. aneurysm neck) so as to at least partially isolate the vascular defect 160 from flow, pressure or both of the patient's vasculature adjacent the vascular defect 160 as shown in FIG. 26. The conformability of the device 10, 210, particularly in the neck region 190 may provide for improved sealing. For some embodiments, once deployed, the permeable shell 40, 240 may substantially slow the flow of fluids and impede flow into the vascular site and thus reduce pressure within the vascular defect 160. For some embodiments, the device 10, 210 may be implanted substantially within the vascular defect 160, however, in some embodiments, a portion of the device 10, 210 may extend into the defect opening or neck 190 or into branch vessels.

For some embodiments, as discussed above, the device 10, 210 may be manipulated by the user to position the device 10, 210 within the vascular site or defect 160 during or after deployment but prior to detachment. For some embodiments, the device 10, 210 may be rotated in order to achieve a desired position of the device 10 and, more specifically, a desired position of the permeable shell 40, 240, prior to or during deployment of the device 10, 210. For some embodiments, the device 10, 210 may be rotated about a longitudinal axis of the delivery system 112 with or without the transmission or manifestation of torque being exhibited along a middle portion of a delivery catheter being used for the delivery. It may be desirable in some circumstances to determine whether acute occlusion of the vascular defect 160 has occurred prior to detachment of the device 10, 210 from the delivery apparatus 111 of the delivery system 112. These delivery and deployment methods may be used for deployment within berry aneurysms, terminal aneurysms, or any other suitable vascular defect embodiments 160. Some method embodiments include deploying the device 10, 210 at a confluence of three vessels of the patient's vasculature that form a bifurcation such that the permeable shell 40 of the device 10, 210 substantially covers the neck of a terminal aneurysm. Once the physician is satisfied with the deployment, size and position of the device 10, 210, the device 10, 210 may then be detached by actuation of the control switch 188 by the methods described above and shown in FIG. 26. Thereafter, the device 10, 210 is in an implanted state within the vascular defect 160 to effect treatment thereof.

Figure 27:
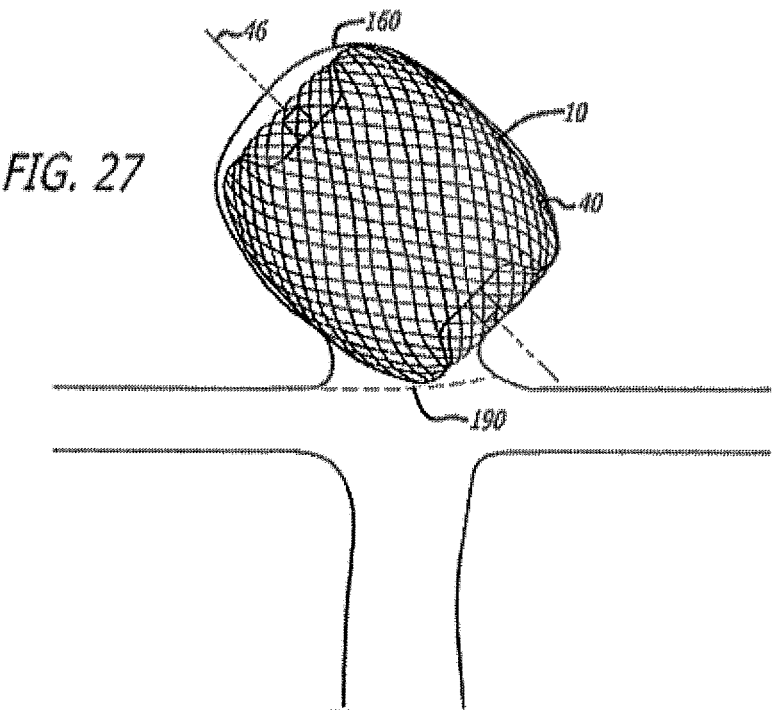
FIG. 27 is an elevation view in partial section of an embodiment of a device for treatment of a patient's vasculature deployed within an aneurysm at a tilted angle.

FIG. 27 illustrates another configuration of a deployed and implanted device in a patient's vascular defect 160. While the implantation configuration shown in FIG. 26 indicates a configuration whereby the longitudinal axis 46 of the device 10, 210 is substantially aligned with a longitudinal axis of the defect 160, other suitable and clinically effective implantation embodiments may be used. For example, FIG. 27 shows an implantation embodiment whereby the longitudinal axis 46 of the implanted device 10, 210 is canted at an angle of about 10 degrees to about 90 degrees relative to a longitudinal axis of the target vascular defect 160. Such an alternative implantation configuration may also be useful in achieving a desired clinical outcome with acute occlusion of the vascular defect 160 in some cases and restoration of normal blood flow adjacent the treated vascular defect. FIG. 28 illustrates a device 10, 210 implanted in an irregularly shaped vascular defect 160. The aneurysm 160 shown has at least two distinct lobes 192 extending from the main aneurysm cavity. The two lobes 192 shown are unfilled by the deployed vascular device 10, 210, yet the lobes 192 are still isolated from the parent vessel of the patient's body due to the occlusion of the aneurysm neck portion 190.

Markers, such as radiopaque markers, on the device 10, 210 or delivery system 112 may be used in conjunction with external imaging equipment (e.g. x-ray) to facilitate positioning of the device or delivery system during deployment. Once the device is properly positioned, the device 10 may be detached by the user. For some embodiments, the detachment of the device 10, 210 from the delivery apparatus 111 of the delivery system 112 may be affected by the delivery of energy (e.g. heat, radiofrequency, ultrasound, vibrational, or laser) to a junction or release mechanism between the device 10 and the delivery apparatus 111. Once the device 10, 210 has been detached, the delivery system 112 may be withdrawn from the patient's vasculature or patient's body 158. For some embodiments, a stent 173 may be place within the parent vessel substantially crossing the aneurysm neck 190 after delivery of the device 10 as shown in FIG. 19 for illustration.

For some embodiments, a biologically active agent or a passive therapeutic agent may be released from a responsive material component of the device 10, 210. The agent release may be affected by one or more of the body's environmental parameters or energy may be delivered (from an internal or external source) to the device 10, 210. Hemostasis may occur within the vascular defect 160 as a result of the isolation of the vascular defect 160, ultimately leading to clotting and substantial occlusion of the vascular defect 160 by a combination of thrombotic material and the device 10, 210. For some embodiments, thrombosis within the vascular defect 160 may be facilitated by agents released from the device 10 and/or drugs or other therapeutic agents delivered to the patient.

For some embodiments, once the device 10, 210 has been deployed, the attachment of platelets to the permeable shell 40 may be inhibited and the formation of clot within an interior space of the vascular defect 160, device, or both promoted or otherwise facilitated with a suitable choice of thrombogenic coatings, anti-thrombogenic coatings or any other suitable coatings (not shown) which may be disposed on any portion of the device 10, 210 for some embodiments, including an outer surface of the filaments 14 or the hubs 66 and 68. Such a coating or coatings may be applied to any suitable portion of the permeable shell 40. Energy forms may also be applied through the delivery apparatus 111 and/or a separate catheter to facilitate fixation and/or healing of the device 10, 210 adjacent the vascular defect 160 for some embodiments. One or more embolic devices or embolic material 176 may also optionally be delivered into the vascular defect 160 adjacent permeable shell portion that spans the neck or opening 190 of the vascular defect 160 after the device 10 has been deployed. For some embodiments, a stent or stent-like support device 173 may be implanted or deployed in a parent vessel adjacent the defect 160 such that it spans across the vascular defect 160 prior to or after deployment of the vascular defect treatment device 10, 210.

In any of the above embodiments, the device 10, 210 may have sufficient radial compliance so as to be readily retrievable or retractable into a typical microcatheter 61. The proximal portion of the device 10, 210, or the device as a whole for some embodiments, may be engineered or modified by the use of reduced diameter filaments, tapered filaments, or filaments oriented for radial flexure so that the device 10, 210 is retractable into a tube that has an internal diameter that is less than about 0.7 mm, using a retraction force less than about 2.7 Newtons (0.6 lbf) force. The force for retrieving the device 10, 210 into a microcatheter 61 may be between about 0.8 Newtons (0.18 lbf) and about 2.25 Newtons (0.5 lbf).

Figure 29:
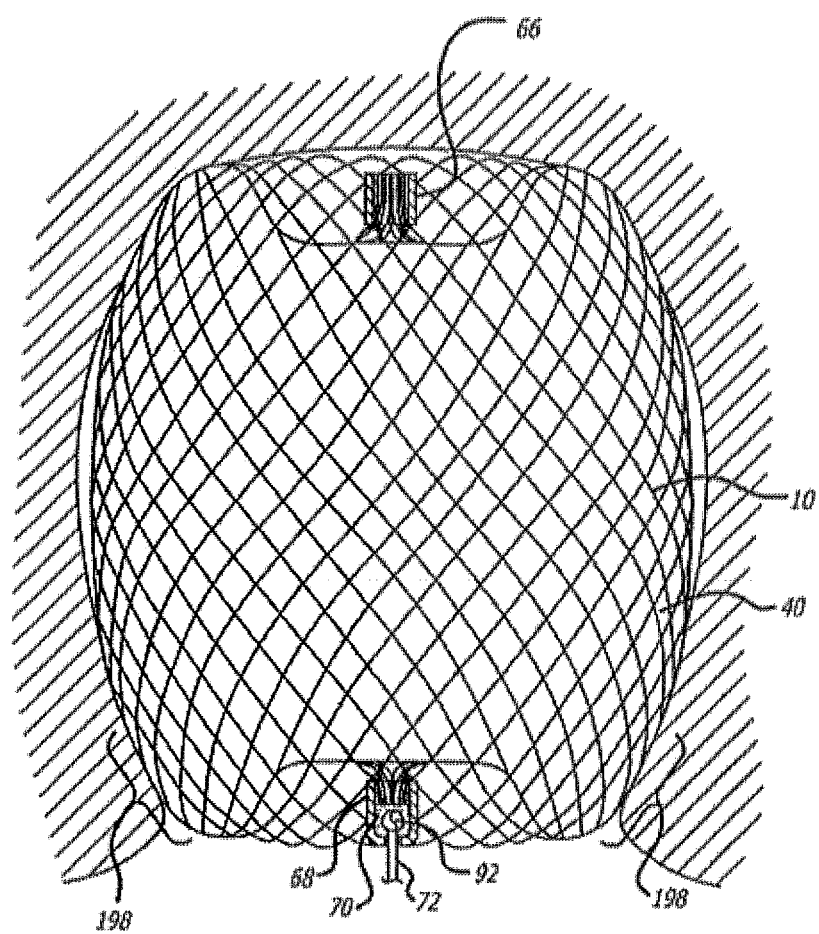
FIG. 29 shows an elevation view in section of a device for treatment of a patient's vasculature deployed within a vascular defect aneurysm.

Engagement of the permeable shell 40, 240 with tissue of an inner surface of a vascular defect 160, when in an expanded relaxed state, may be achieved by the exertion of an outward radial force against tissue of the inside surface of the cavity of the patient's vascular defect 160, as shown for example in FIG. 29. A similar outward radial force may also be applied by a proximal end portion and permeable shell 40, 240 of the device 10, 210 so as to engage the permeable shell 40 with an inside surface or adjacent tissue of the vascular defect 160. Such forces may be exerted in some embodiments wherein the nominal outer transverse dimension or diameter of the permeable shell 40 in the relaxed unconstrained state is larger than the nominal inner transverse dimension of the vascular defect 160 within which the device 10, 210 is being deployed, i.e., oversizing as discussed above. The elastic resiliency of the permeable shell 40 and filaments 14 thereof may be achieved by an appropriate selection of materials, such as superelastic alloys, including nickel titanium alloys, or any other suitable material for some embodiments. The conformability of a proximal portion of the permeable shell 40, 240 of the device 10, 210 may be such that it will readily ovalize to adapt to the shape and size of an aneurysm neck 190, as shown in FIGS. 20-22, thus providing a good seal and barrier to flow around the device. Thus, the device 10 may achieve a good seal, substantially preventing flow around the device without the need for fixation members that protrude into the parent vessel.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A device for treatment of a patient's cerebral aneurysm, comprising:
    a first permeable shell including a radially constrained elongated state configured for delivery within a catheter lumen, an expanded state with a longitudinally shortened configuration relative to the radially constrained state, and a plurality of elongate filaments that are woven together to form a mesh, the expanded state having a proximal portion, a distal portion, and an interior cavity, wherein each of the plurality of filaments has a proximal end and a distal end, and wherein the proximal ends of each of the plurality of filaments are gathered by a proximal hub and the distal ends of each of the plurality of filaments are gathered by a distal hub; and
    a second permeable shell including a radially constrained elongated state configured for delivery within a catheter lumen, an expanded state with a longitudinally shortened configuration relative to the radially constrained state of the second permeable shell, and a plurality of elongate filaments that are woven together to form a mesh, wherein at least a portion of the second permeable shell is in contact with the proximal portion of the first permeable shell, wherein each of the plurality of filaments of the second permeable shell has a proximal end and a distal end, wherein the second permeable shell is stiffer than the first permeable shell,
    wherein the proximal ends of each of the plurality of filaments of the second permeable shell are gathered in the proximal hub with the proximal ends of each of the plurality of filaments of the first permeable shell, and
    wherein a length of the expanded state of the second permeable shell is smaller than a length of the expanded state of the first permeable shell.

2. The device of claim 1, wherein an outer surface of the second permeable shell is in contact with an inner surface of the first permeable shell.

3. The device of claim 1, wherein the length of the expanded state of the second permeable shell is between about 10% to about 40% of the length of the expanded state of the first permeable shell.

4. The device of claim 1, wherein the second permeable shell is attached to the first permeable shell by welding, adhesive, or mechanical ties.

5. The device of claim 1, wherein the distal ends of each of the plurality of filaments of the second permeable shell are not bound together.

6. The device of claim 1, wherein a diameter of each of the plurality of filaments of the second permeable shell is larger than a diameter of each of the plurality of filaments of the first permeable shell.

7. A device for treatment of a patient's cerebral aneurysm, comprising:
    a first self-expanding mesh including a radially constrained elongated state configured for delivery within a catheter lumen, an expanded state with a longitudinally shortened configuration relative to the radially constrained state, and a plurality of elongate filaments that are woven together to form the first self-expanding mesh, the expanded state having a proximal portion, a distal portion, and an interior cavity, wherein each of the plurality of filaments has a proximal end and a distal end, and wherein the proximal ends of each of the plurality of filaments are gathered by a proximal hub and the distal ends of each of the plurality of filaments are gathered by a distal hub; and
    a second self-expanding mesh including a radially constrained elongated state configured for delivery within a catheter lumen, an expanded state with a longitudinally shortened configuration relative to the radially constrained state of the second permeable shell, and a plurality of elongate filaments that are woven together to form the second self-expanding mesh, wherein at least a portion of the second self-expanding mesh is in contact with the proximal portion of the first self-expanding mesh, wherein each of the plurality of filaments of the second permeable shell has a proximal end and a distal end, wherein the second self-expanding mesh is stiffer than the first self-expanding mesh,
    wherein the proximal ends of each of the plurality of filaments of the second self-expanding mesh are gathered in the proximal hub with the proximal ends of each of the plurality of filaments of the first self-expanding mesh, and
    wherein a length of the expanded state of the second self-expanding mesh is smaller than a length of the expanded state of the first self-expanding mesh.

8. The device of claim 7, wherein an outer surface of the second self-expanding mesh is in contact with an inner surface of the first self-expanding mesh.

9. The device of claim 7, wherein the length of the expanded state of the second self-expanding mesh is between about 10% to about 40% of the length of the expanded state of the first self-expanding mesh.

10. The device of claim 7, wherein the second self-expanding mesh is attached to the first self-expanding mesh by welding, adhesive, or mechanical ties.

11. The device of claim 7, wherein the distal ends of each of the plurality of filaments of the second self-expanding mesh are not bound together.

12. The device of claim 7, wherein a diameter of each of the plurality of filaments of the second self-expanding mesh is larger than a diameter of each of the plurality of filaments of the first self-expanding mesh.

13. A device for treatment of a patient's cerebral aneurysm, comprising:
- a first permeable shell including a radially constrained elongated state configured for delivery within a catheter lumen, an expanded state with a longitudinally shortened configuration relative to the radially constrained state, and a plurality of elongate filaments that are woven together to form a mesh, the expanded state having a proximal portion, a distal portion, and an interior cavity, wherein each of the plurality of filaments has a proximal end and a distal end, and wherein the proximal ends of each of the plurality of filaments are gathered by a proximal hub and the distal ends of each of the plurality of filaments are gathered by a distal hub; and
- a second permeable shell including a radially constrained elongated state configured for delivery within a catheter lumen, an expanded state with a longitudinally shortened configuration relative to the radially constrained state of the second permeable shell, and a plurality of elongate filaments that are woven together to form a mesh, wherein at least a portion of the second permeable shell is in contact with the proximal portion of the first permeable shell, wherein each of the plurality of filaments of the second permeable shell has a proximal end and a distal end,
wherein the second permeable shell has an open distal end, and wherein a length of the expanded state of the second permeable shell is smaller than a length of the expanded state of the first permeable shell.

14. The device of claim 13, wherein the second permeable shell is stiffer than the first permeable shell.

15. The device of claim 13, wherein the second permeable shell is attached to the first permeable shell by welding, adhesive, or mechanical ties.

16. The device of claim 13, wherein the distal ends of each of the plurality of filaments of the second permeable shell are not attached to the first permeable shell.

17. The device of claim 13, wherein the proximal ends of each of the plurality of filaments of the second permeable shell are gathered in the proximal hub with the proximal ends of each of the plurality of filaments of the first permeable shell.

18. The device of claim 13, wherein a diameter of each of the plurality of filaments of the second permeable shell is larger than a diameter of each of the plurality of filaments of the first permeable shell.

* * * * *